(12) United States Patent
Shykind et al.

(10) Patent No.: US 11,879,892 B2
(45) Date of Patent: Jan. 23, 2024

(54) SYSTEM, APPARATUS AND METHOD FOR SENSING, DETECTING AND EFFECTING IN A MICRO-TO-NANO ENVIRONMENT

(71) Applicant: Velanidi Technologies LLC, Portland, OR (US)

(72) Inventors: David Nathan Shykind, Buxton, OR (US); Devin Thomas Wiley, Hillsboro, OR (US)

(73) Assignee: VELANIDI TECHNOLOGIES LLC, Portland, OR (US)

( * ) Notice: Subject to any disclaimer, the term of this patent is extended or adjusted under 35 U.S.C. 154(b) by 773 days.

(21) Appl. No.: 16/841,456

(22) Filed: Apr. 6, 2020

(65) Prior Publication Data
US 2020/0319165 A1    Oct. 8, 2020

Related U.S. Application Data

(60) Provisional application No. 62/830,762, filed on Apr. 8, 2019.

(51) Int. Cl.
*A61K 9/00* (2006.01)
*G01N 33/50* (2006.01)
(Continued)

(52) U.S. Cl.
CPC ......... *G01N 33/5091* (2013.01); *A61K 49/00* (2013.01); *G01N 27/4065* (2013.01); *G01N 27/4148* (2013.01); *A61N 1/325* (2013.01)

(58) Field of Classification Search
CPC ............... A61N 1/325; G01N 27/4065; G01N 27/4148; A61K 9/00
See application file for complete search history.

(56) References Cited

U.S. PATENT DOCUMENTS

2005/0048651 A1* 3/2005 Ryttsen .................. C12M 35/02
                                                                435/459
2008/0047926 A1    2/2008 Santini, Jr.
(Continued)

OTHER PUBLICATIONS

International Application No. PCT/US20/26923, International Search Report and Written Opinion, dated Sep. 4, 2020.
(Continued)

*Primary Examiner* — Deanna K Hall
(74) *Attorney, Agent, or Firm* — MARSHALL, GERSTEIN & BORUN LLP

(57) ABSTRACT

An apparatus that is μm- or nm-scale in size and can include integrated circuitry logic based on sub 10 nm SIA transistor nodes, a sensing subsystem, a deciding subsystem, an effecting subsystem, and a power harvesting system is described. The sensing subsystem can identify pathogenic entities, including disease associated cells (for example, cancer cells, autoimmune cells, or pathological microbes) or viruses. The sensing subsystem can include at least one pad constructed of an electrically conductive material and linkers attached to the at least one pad. Each linker can also be attached to a targeting agent (for example, an antibody fragment) or a reference agent. Upon the binding of a targeting agent with an entity of interest, the information is transferred to the logic circuitry, which processes the binding event information and decides whether the entity is disease associated (e.g., a disease associated cell or virus) and requires delivery of therapeutic agents or other treatment.

24 Claims, 23 Drawing Sheets

(51) Int. Cl.
  *G01N 27/406* (2006.01)
  *G01N 27/414* (2006.01)
  *A61K 49/00* (2006.01)
  *A61N 1/32* (2006.01)

(56) References Cited

U.S. PATENT DOCUMENTS

| | | | |
|---|---|---|---|
| 2011/0230736 A1* | 9/2011 | Tepper | A61B 5/14532 604/93.01 |
| 2015/0168337 A1 | 6/2015 | Soleymani et al. | |
| 2017/0306284 A1 | 10/2017 | Yamanishi et al. | |
| 2019/0090801 A1 | 3/2019 | Rogers et al. | |
| 2020/0319165 A1 | 10/2020 | Shykind et al. | |

OTHER PUBLICATIONS

Agard et al., A strain-promoted [3+2] azide-alkyne cycloaddition for covalent modification of biomolecules in living systems, J. Am. Chem. Soc., 126(46):15046-7 (2004).
Aragonès et al., Measuring the Spin-Polarization Power of a Single Chiral Molecule. Small, 13, 1602519-1602524 (2017).
Arnold et al., DNA charge transport: from chemical principles to the cell. Cell Chem. Biol. 23:183-197 (2016).
Beall et al., Effects of the Backbone and Chemical Linker on the Molecular Conductance of Nucleic Acid Duplexes. J. Am. Chem. Soc. 139, 6726-6735 (2017).
Beratan, Why are DNA and Protein Electron Transfer So Different? Annu. Rev. Phys. Chem. 70, 71-97 (2019).
Chan et al., Polytriazoles as copper(I)-stabilizing ligands in catalysis, Org. Lett., 6(17):2853-5 (2004).
Dien et al., Progress Toward a Semi-Synthetic Organism with an Unrestricted Expanded Genetic Alphabet. J. Am. Chem. Soc. 140, 16115-16123 (2018).
Fantoni et al., A hitchhiker's guide to click-chemistry with nucleic acids, Chem. Rev., 121(12):7122-54 (2021).
Furuhata et al., Highly Conductive Nucleotide Analogue Facilitates Base-Calling in Quantum-Tunneling-Based DNA Sequencing. ACS Nano 13, 5028-5035 (2019).
Genereux et al., Mechanisms for DNA charge transport. Chem. Rev. 110:1642-62 (2010).
Hauser et al., Utilising the left-helical conformation of L-DNA for analysing different marker types on a single universal microarray platform, Nucleic Acids Res., 34(18):5101-11 (2006).
Hoshika et al., Hachimoji DNA and RNA: A genetic system with eight building blocks, Science, 363(6429):884-7 (2019).
Hueberger et al., An Alternative Nucleobase Code: Characterization of Purine-Purine DNA Double Helices Bearing Guanine-Isoguanine and Diaminopurine 7 Deaza Xanthine Base Pairs. ChemBioChem, 9, 2779-2783 (2008).
International Aplication No. PCT/US2021/030038, International Search Report and Written Opinion, dated Sep. 9, 2021.
Kawai et al., Hole transfer in LNA and 5-Me-2'-deoxyzebularine-modified DNA, J. Am. Chem. Soc., 134(22):9406-9 (2012).
Kawai et al., Hole Transfer Kinetics of DNA. Acc. Chem. Res. 46, 2616-2625 (2013).
Kawai et al., HOMO Energy Gap Dependence of Hole-Transfer Kinetics in DNA. J. Am. Chem. Soc. 134, 4806-4811 (2012).
Kawai et al., Long-Range Charge Transfer through DNA by Replacing Adenine with Diaminopurine. J. Am. Chem. Soc. 132, 627-630 (2010).
Kiran et al., Helicenes—A New Class of Organic Spin Filter. Adv. Mater. 28, 1957-1962 (2016).
Kolb et al., Click Chemistry: Diverse chemical function from a few good reactions, Angew Chem Int. Ed., 40:2004-21 (2001).
Kolb et al., The growing impact of click chemistry on drug discovery, DDT, 8(24):1128-37 (2003).
Lewis et al., Click chemistry in situ: acetylcholinesterase as a reaction vessel for the selective assembly of a femtomolar inhibitor from an array of building blocks, Angew Chem Int Ed Engl., 41(6):1053-7 (2002).
Li et al., Natural-like Replication of an Unnatural Base Pair for the Expansion of the Genetic Alphabet and Biotechnology Applications. J. Am. Chem. Soc. 136, 826-829 (2014).
Liu et al., Size-Expanded Analogues of dG and dC: Synthesis and Pairing Properties in DNA. J. Org. Chem. 70, 639-647 (2005).
Liu et al., Toward a New Genetic System with Expanded Dimensions: Size-Expanded Analogues of Deoxyadenosine and Thymidine. J. Am. Chem. Soc. 126, 1102-1109 (2004).
Manetsch et al., In situ click chemistry: Enzyme inhibitors made to their own specifications, J Am Chem Soc., 126:12809-18 (2004).
Nakatani et al., Modulation of DNA-Mediated Hole-Transport Efficiency by Changing Superexchange Electronic Interaction. J. Am. Chem. Soc. 122, 5893-5894 (2000).
Rostovtsev et al., A stepwise huisgen cycloaddition process: copper(I)-catalyzed regioselective "ligation" of azides and terminal alkynes, Angew Chem Int Ed Engl., 41(14):2596-9 (2002).
Speers et al., Activity-based protein profiling in vivo using a copper(i)-catalyzed azide-alkyne [3+2] cycloaddition, J. Am. Chem. Soc., 125(16):4686-7 (2003).
Tang et al., DNA-directed assembly of protein microarrays, Frontiers in Bioscience, 13(13):5755-71 (2008).
Tornøe et al., Peptidotriazoles on solid phase: [1,2,3]-triazoles by regiospecific copper(i)-catalyzed 1,3-dipolar cycloadditions of terminal alkynes to azides, J. Org. Chem., 67(9):3057-64 (2002).
Waser et al., Cobalt-catalyzed hydroazidation of olefins: convenient access to alkyl azides, J. Am. Chem. Soc., 127(23):8294-5 (2005).
Wierzbinski et al., Effect of Backbone Flexibility on Charge Transfer Rates in Peptide Nucleic Acid Duplexes. J. Am. Chem. Soc. 134, 9335-9342 (2012).
Winnacker et al., Artificial genetic sets composed of size-expanded base pairs, Angew. Chem. Int. Ed., 52:12498-508 (2013).
Young et al., Mirror-image oligonucleotides: history and emerging applications, Chem. Eur. J., 25:7981-90 (2019).
Zhang et al., Ruthenium-catalyzed cycloaddition of alkynes and organic azides, J Am Chem Soc., 127:15998-9 (2005).
Zhu et al., Switchable DNA wire: deposition-stripping of copper nanoclusters as an "On-Off" nanoswitch, Scientific Reports, 6(1):19515 (2016).

* cited by examiner

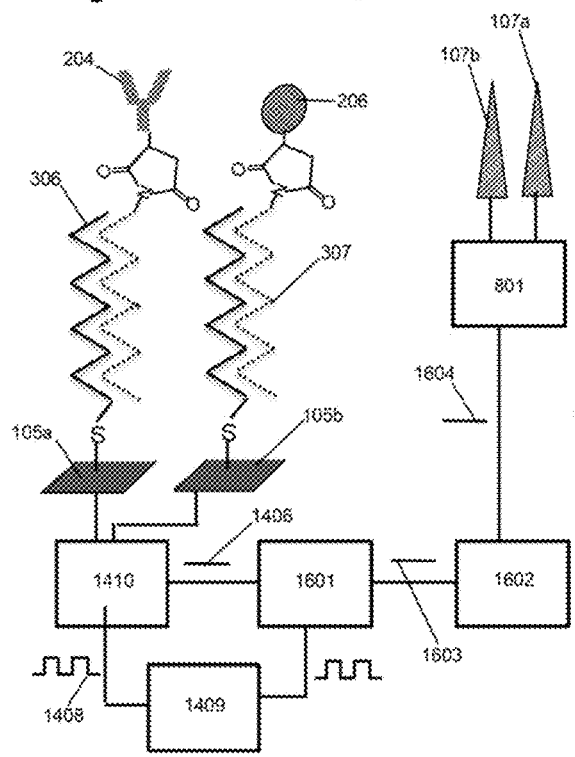 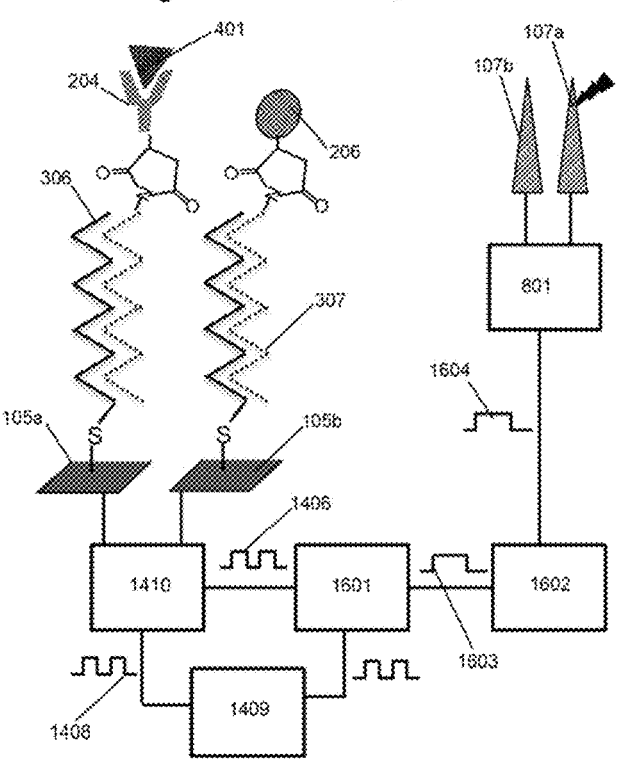

FIG. 20
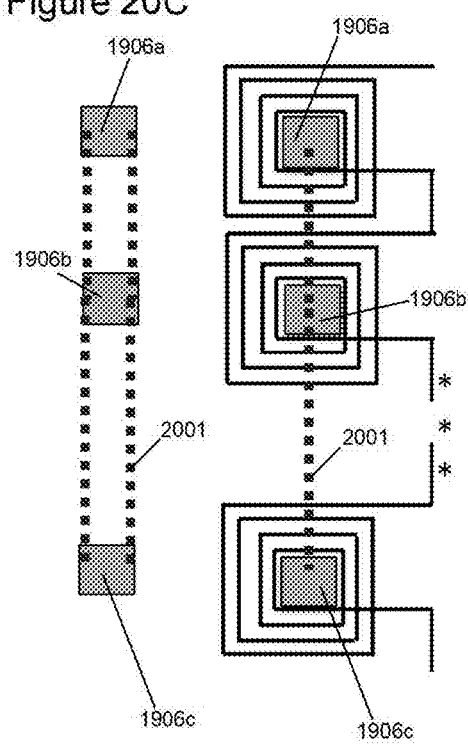
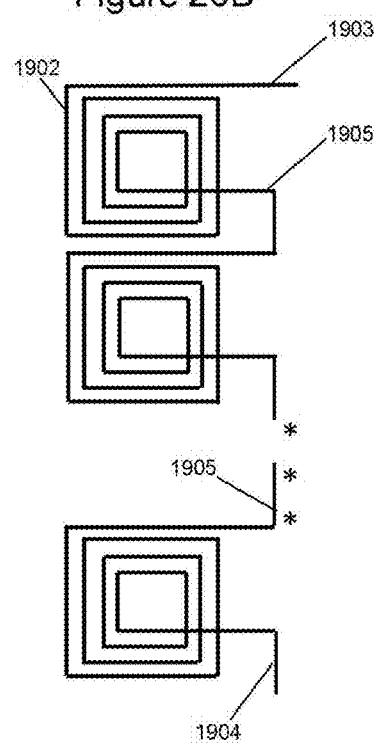
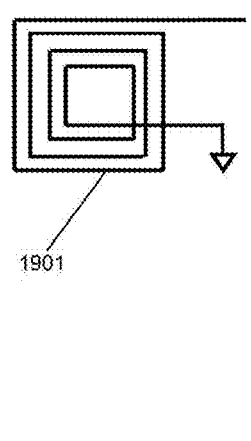

FIG. 21
Figure 21A
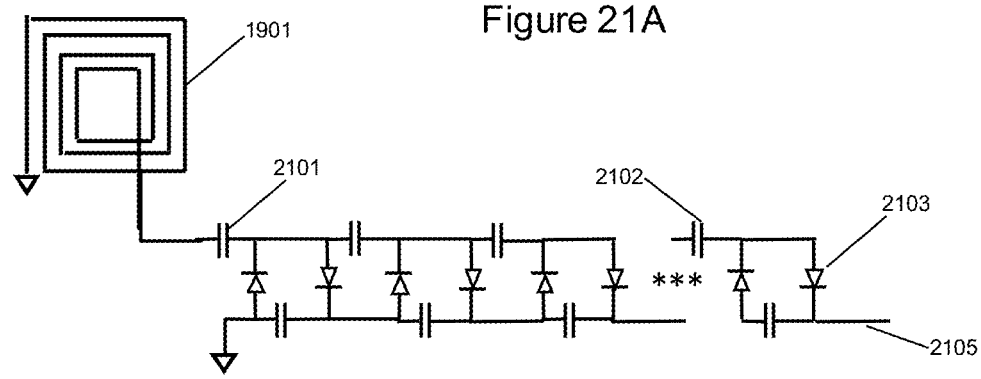
Figure 21B
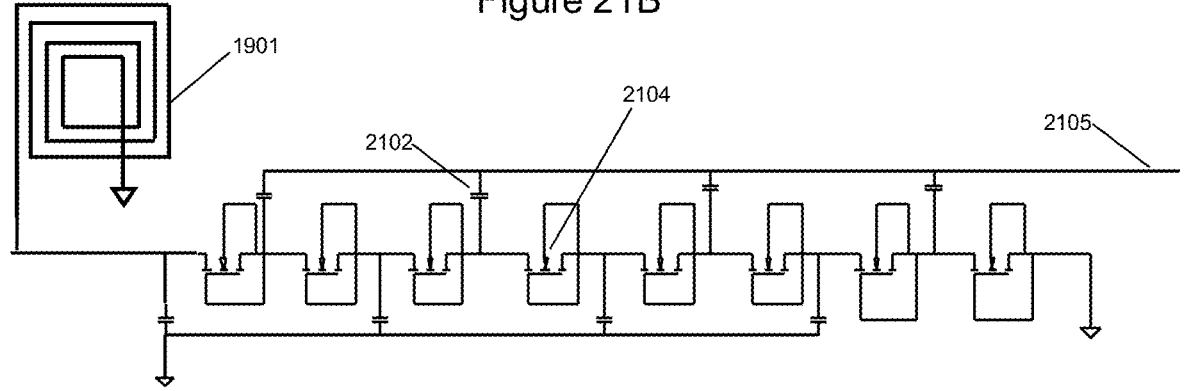

FIG. 23
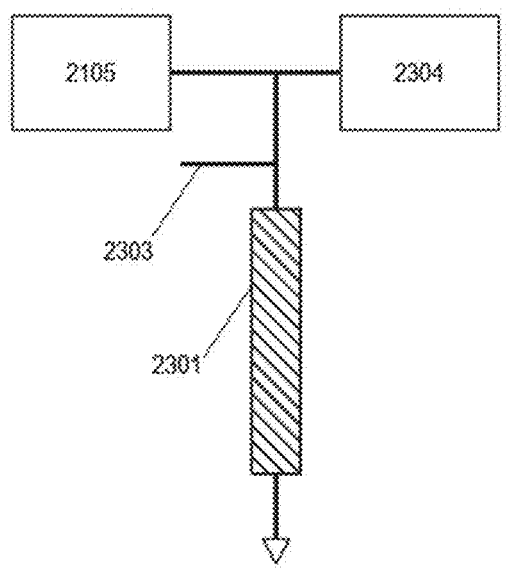
Figure 23A
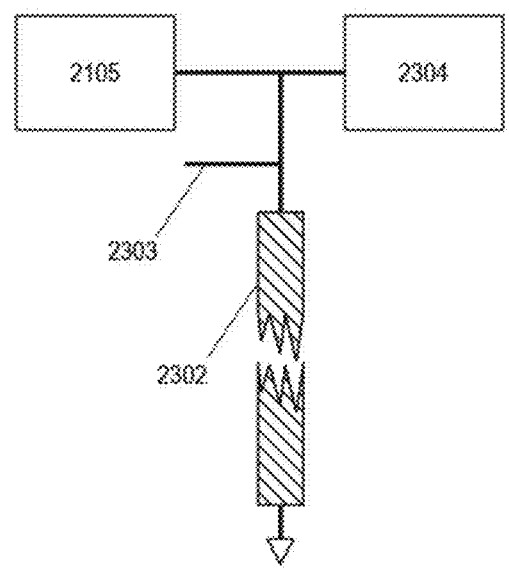
Figure 23B

SYSTEM, APPARATUS AND METHOD FOR SENSING, DETECTING AND EFFECTING IN A MICRO-TO-NANO ENVIRONMENT

CROSS REFERENCE TO RELATED APPLICATIONS

This application claims the benefit of U.S. Provisional Patent Application Ser. No. 62/830,762 filed on Apr. 8, 2019 which is hereby incorporated by reference in its entirety.

FIELD OF THE INVENTION

This invention relates to therapeutic or medicinal nanorobots, including nano- or micro-devices that sense and identify chemical and biological materials and can dispense targeted therapeutics and other chemicals.

BACKGROUND OF THE INVENTION

Diseases in which pathogenic entities, including disease associated cells ("DACs") and pathogenic viruses, are at the root of a pathologic mechanism are a broad and major cause of morbidity and mortality. This category of diseases is comprised of, but not limited to, cancers, autoimmune diseases, and infectious diseases (including those caused by viruses, parasites, bacteria, and others). Cancer alone in 2019 resulted in the deaths of roughly 600,000 people in the United States, and there were an estimated 1.8 million new cancer diagnoses. A similar trend, in both high economic cost and disease prevalence and mortality, is seen in autoimmune diseases and infectious diseases, as well as the highly prevalent cardiovascular diseases, neurologic diseases, and metabolism-related diseases (e.g. metabolic syndrome, obesity, diabetes).

A major reason for the lack of progress in developing efficacious and definitive therapeutics that target pathogenic entities (including DACs, parasites, viruses and others) is the innate ability of these pathogenic entities to adapt and develop resistance mechanisms that render many therapeutics inutile. There is now growing concern for infectious diseases that are becoming resistant even to the most advanced antibiotics. The ability of pathogens to adapt resistance mechanisms to antibiotics has created a continuous need to develop new antibiotic strategies. Moreover, there is an ever-present threat that we will encounter new resistant strains of microbes or viruses that are untreatable, and that will effectively force medicine into a pre-penicillin and pre-therapeutic era. Although there has been much effort over the past century in developing new small molecule, biologic, and nanoparticle-based therapeutics to neutralize pathogenic entities (including against DACs, parasites, and viruses), there is yet to emerge a viable technology that can act on treatment-resistant cells. Of all of the treatment modalities that have been developed to date, almost all attempt to take advantage of some biologic process—processes for which pathogenic entities (including DACs, parasites and viruses) have had epochs to evolve with counteracting resistant mechanisms. This disclosure describes a logic-based and non-biomimetic effector system, apparatus and method for neutralizing pathogenic entities, for which no corresponding resistance can develop.

With the advent of precision medicine, such as chimeric antigen receptor T cell (CAR-T) therapy, clustered regularly interspaced short palindromic repeats ("CRISPR"), siRNA, and other gene therapies, there are new growing problems in the ability to safely treat specific cell types, sparing the patient of off target effects and pathologic activation of the immune system as is the case in viral-vector-associated gene therapy and CAR-T therapy. New solutions are going to be needed to not just improve the precision of these medicines, but also enable these medicines to be delivered to specific pathogenic entities (including DACs and viruses), which will reduce the potential toxicities of these medicines (off-target effects) and significantly improve their efficacy with high concentrations released locally at the pathogenic entity through delivery of a therapeutic or therapeutic action directly to the pathogenic entity. This disclosure describes how to deliver any therapeutic or imaging agent only to a pathogenic entity of interest (e.g. only to a DAC such as a cancer cell), facilitate the entry of that agent into specific DACs regardless of therapeutic or imaging agent size or chemical composition, and reduce pathologic immune activation and other toxic off-target effects.

This disclosure describes a system, apparatus and method that can accomplish this highly specific therapeutic delivery within a biological system, including but not limited to humans. Finally, this disclosure describes embodiments that include usages that stretch beyond traditional therapeutic and imaging applications. As set forth herein, particular embodiments of the subject matter described herein could be used as sensors, chemical synthesis tools, and delivery agents, and they could be used to communicate gathered information to external sensors or within the particular embodiments, with or without necessarily being introduced within a biologic or in-vivo system.

BRIEF SUMMARY OF THE INVENTION

In one embodiment, a MNSDED includes a non-conductive housing having a surface and that contains supporting logic circuitry. At least one electrically conductive needle extending from the housing is provided, with the needle connected to the logic circuitry and to a needle driving circuit. At least one electrically conductive pad is positioned on the housing surface and connected to the logic circuitry and to at least one targeting agent capable of interacting with a target. In response to target interaction, the logic circuitry allows voltage from the needle driving circuit to be applied to the at least one needle.

In one embodiment, the non-conductive housing of a MNSDED has a major axis length from 100 nanometers to 500 microns and logic circuitry that is manufactured using a 10 nm or less SIA transistor node.

In one embodiment, a biocompatible protective agent surrounding at least a portion of the surface of the non-conductive housing is provided.

In one embodiment, each targeting agent is connected to an electrically conductive linker, with the electrically conductive linker being attached to the electrically conductive pad.

In one embodiment, the at least one needle is able to interact electrically with a bilipid layer of a target cell that is attached to the targeting agent, and sufficient voltage from the needle driving circuit is available to promote at least one of ablation and electroporation of the target cell.

In one embodiment, a MNSDED includes a housing having a surface and that contains supporting logic circuitry and a biocompatible protective agent surrounding at least a portion of the surface. At least one electrically conductive pad is positioned on the housing surface and connected to the logic circuitry and to a targeting agent capable of interacting with a target. A reservoir is configured in the housing to hold at least one of a therapeutic agent and a diagnostic agent. In response to target interaction with the targeting agent, the logic circuitry can initiate release of the at least one of a therapeutic agent and diagnostic agent.

In one embodiment, a release barrier that prevents release of the at least one of a therapeutic agent and diagnostic agent until electrically activated by the logic circuitry is provided. The release barrier can include a thermoresponsive material that dissolves when electrically activated by the logic circuitry. Alternatively or in addition, the release barrier can include a material that dissolves when placed in proximity to a target cell.

In one embodiment, a MNSDED includes a housing having a surface and that contains supporting logic circuitry. A first electrically conductive pad is positioned on the housing surface and connected both to the logic circuitry and to a first electrically conductive linker also attached to a targeting agent capable of interacting with a target. A second electrically conductive pad is positioned on the housing surface and connected both to the logic circuitry and to a second electrically conductive linker attached to a reference agent incapable of interacting with the target. In response to target interaction with the targeting agent, the logic circuitry can initiate an effector mechanism.

In one embodiment, in response to target interaction with the targeting agent, a sense amplifier connected to the first pad and the second pad is triggered, and deciding logic circuitry can promote at least one of ablation and electroporation of the target or initiate release of at least one of a therapeutic agent and diagnostic agent from a reservoir.

In one embodiment, a MNSDED includes a housing having a surface and that contains supporting logic circuitry. A biocompatible protective agent surrounding at least a portion of the surface is provided. At least one electrically conductive pad is positioned on the housing surface and connected to the logic circuitry and to a targeting agent capable of interacting with a target. A gasket surrounding the at least one electrically conductive pad is further provided.

In one embodiment, the gasket promotes binding of the targeting agent when the targeting agent interacts with the target. The gasket can be formed from molecules that extend longer than molecules forming the biocompatible protective agent.

In one embodiment, the gasket boundary is printed on the MNSDED surface around the at least one electrically conductive pad using bio-safe lithography.

In one embodiment, a MNSDED includes non-conductive housing having a surface and that contains supporting logic circuitry. An antenna is supported by the non-conductive housing and is connected to an energy harvesting circuit to power the logic circuitry and voltage amplifier circuitry. At least one electrically conductive pad is positioned on the housing surface and connected to the logic circuitry and to a targeting agent capable of interacting with a target.

In one embodiment, the antenna further comprises a multi turn and multilayer coil. In addition to energy harvesting circuitry, an antenna or antennas can be further connected to signaling circuitry.

In one embodiment, a MNSDED includes non-conductive housing having a surface and that contains supporting logic circuitry. An antenna is supported by the non-conductive housing and connected to a signaling circuit connected to the logic circuitry. At least one electrically conductive pad is positioned on the housing surface and connected to the logic circuitry and to a targeting agent capable of interacting with a target.

In one embodiment, the signaling circuit can enable communication with an external transceiver. Alternatively or in addition, the signaling circuit can enable communication with another MNSDED.

In one embodiment, a method of treating disease associated cells (DACs) includes introducing into a patient a plurality of MNSDEDs, each MNSDED having a non-conductive housing having a surface and that contains supporting logic circuitry and at least one electrically conductive needle extending from the housing. The needle is connected to the logic circuitry and to a needle driving circuit, and further includes at least one electrically conductive pad positioned on the housing surface and connected to the logic circuitry and a targeting agent capable of interacting with a DAC. In response to DAC and MNSDED interaction via the targeting agent, a voltage is applied from the needle driving circuit to the at least one needle to ablate the DAC.

In one embodiment, a method of treating pathogenic entities, including disease associated cells (DACs) and pathogenic viruses, includes introducing into a patient a plurality of MNSDEDs, each MNSDED having a non-conductive housing having a surface and that contains supporting logic circuitry. A reservoir is configured in the housing to hold at least one of a therapeutic agent and a diagnostic agent, with the reservoir connected to the logic circuitry. At least one electrically conductive pad is positioned on the housing surface and connected to the logic circuitry and a targeting agent capable of interacting with a pathogenic entity. In response to pathogenic entity and MNSDED interaction via the targeting agent, using the logic circuitry can initiate release of the at least one of a therapeutic agent and diagnostic agent. Alternatively or in addition, applying voltage from the needle driving circuit to the at least one needle can porate the DAC and permit entry of the at least one of a therapeutic agent and diagnostic agent into the DAC.

In one embodiment, testable MNSDED system includes a wafer including a plurality of housings configured to have an attached biocompatible coating, with each housing having a surface and including a substrate supporting sub 10 nm transistor logic circuitry. At least one electrically conductive test pad is positioned on the surface and connected to the logic circuitry. A plurality of separate test logic circuits can be positioned adjacent to the each of the plurality of housings and respectively connected to the respective electrically conductive test pads.

In one embodiment, a therapeutic composition includes a pharmaceutically acceptable carrier and a plurality MNSDEDs contained within the carrier. The MNSDEDs include a non-conductive housing having a surface and that contains supporting logic circuitry. At least one electrically conductive needle extends from the housing, with the needle connected to the logic circuitry and to a needle driving circuit. At least one electrically conductive pad is positioned on the housing surface and is connected to the logic circuitry and to a targeting agent capable of interacting with a target.

In one embodiment, a therapeutic composition includes a pharmaceutically acceptable carrier and a plurality MNSDEDs contained within the carrier. The MNSDEDs includes a housing having a surface and that contains supporting logic circuitry and has a biocompatible protective agent surrounding at least a portion of the surface. At least one electrically conductive pad is positioned on the housing surface and connected to the logic circuitry and to a targeting agent capable of interacting with a target. A reservoir is configured in the housing to hold at least one of a therapeutic agent and a diagnostic agent.

In one embodiment, a method of treating disease associated cells (DACs) includes introducing into a patient a plurality of MNSDEDs, each MNSDED having a non-conductive housing having a surface and that contains supporting logic circuitry and further comprising at least one electrically conductive pad positioned on the housing surface that is connected to the logic circuitry and at least one targeting agent capable of interacting with a targeted DAC. After association of the at least one targeting agent with a DAC, the MNSDEDs are powered using an antenna connected to the logic circuitry. Using a sensing subsystem circuitry within each of the MNSDEDs, a signal can be generated to indicate binding of the at least one targeting agent with a targeted DAC. Then, a deciding subsystem within each MNSDED can determine if binding of the at least one targeting agent has been made with a targeted DAC, based on one or more inputs or signals received from the sensing subsystem. If the deciding subsystem logic circuitry determines that the MNSDED is bound to the predetermined DAC, an effecting subsystem can be activated to direct current to at least one of a nanoneedle and reservoir associated circuitry for each bound MNSDED.

In one embodiment, a MNSDED can include a non-conductive housing having a surface and that contains supporting logic circuitry. At least one electrically conductive pad is positioned on the housing surface and connected to the logic circuitry. At least one targeting agent is capable of interacting with a target and at least one electrically conductive linker connecting each targeting agent with an electrically conductive pad is provided. The MNSDED has a biocompatible protective agent surrounding at least a portion of the surface of the non-conductive housing and the zeta potential of the MNSDED is between 0 mV to −20 mV.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings. In accord with common practice, the various illustrated features in the drawings are not to scale but are drawn to emphasize specific features relevant to the invention. Moreover, the sizes of features and the thicknesses of layers may depart substantially from the scale with which these are shown.

FIGS. 16A-16B illustrate a schematic representation of the MNSDED binding detection process.

FIGS. 20A-20C illustrate details of an embodiment of the RFEHC coil design.

FIGS. 21A-21B illustrate an embodiment of voltage multiplier circuits connected to RFEHC LC (coil-capacitor) circuits.

FIGS. 23A-23B illustrate a schema for testing and enabling only those MNSDEDs which pass a set of logic tests to function.

DETAILED DESCRIPTION OF THE INVENTION

Figure 1:
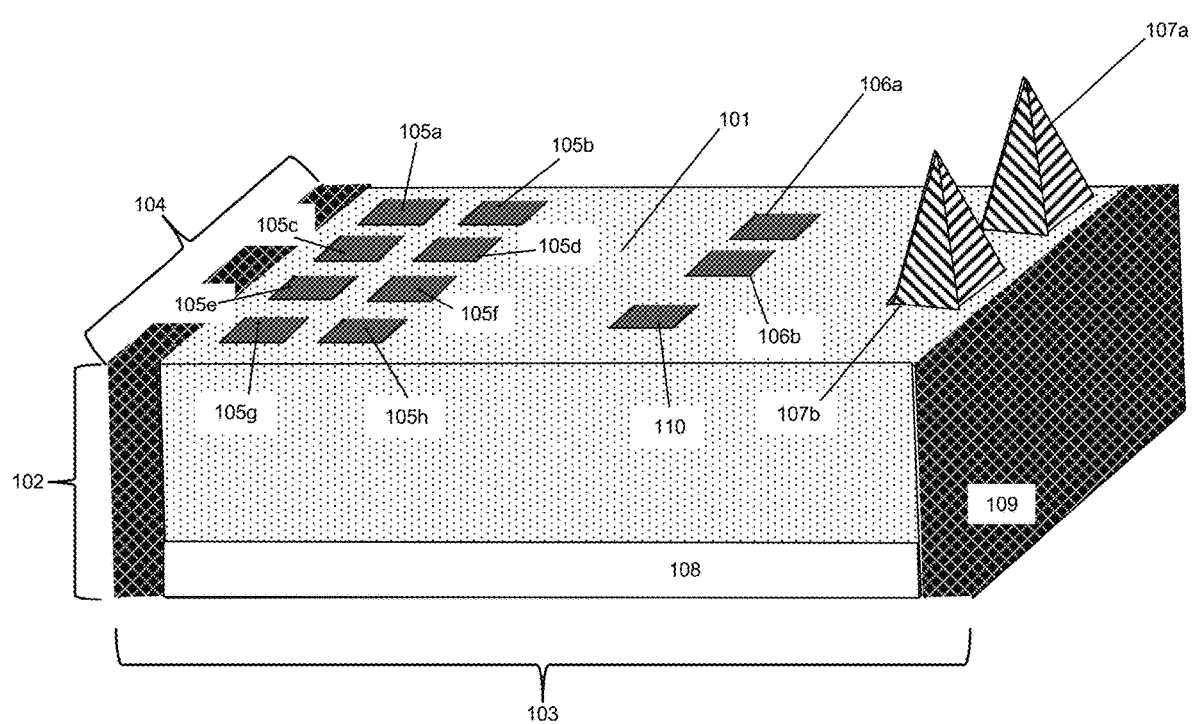
FIG. 1 illustrates an exemplary geometry of a MNSDED.

Described herein are methods for fabricating and utilizing one or more micro/nano-sensing-deciding-effecting-devices ("MNSDEDs"), as well as a description of the constituent MNSDED components including: bar-code targeting recognition (e.g. multiple unique targeting ligands that, upon binding to DAC receptors, results in an electronic signal that activates or deactivates an effector mechanism), integrated circuits (e.g. NANDs, current mirrors, differential amplifiers), effector mechanisms (e.g. electroporating nano-needles, therapeutic release modules), power source (e.g. inductive power transfer via RF antenna), and other components that will be described in detail herein. The structure and manner by which these constituent MNSDED components are interconnected and interoperate also are described herein.

Also described herein are examples of specific MNSDED designs, related compositions, and methods of delivery that can be used in concert for specific therapeutic and non-therapeutic applications. These designs, compositions, and methods will describe how MNSDEDs (or compounds of interest contained in the MNSDEDs), upon administration to a subject, may detect, neutralize, eliminate, or treat pathogenic entities (including DACs and viruses). Additionally, methods of use will be described by which MNSDEDs could be used as chemical sensors, chemical synthesis tools, and chemical delivery agents, without necessarily being introduced within a biologic or in-vivo system.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the term "about", when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

The term "attach," "attached" or "attachment" as used herein, refers to connecting or uniting by a chemical bond, link, or force in order to keep two or more components together.

As used herein, "for example," "for instance," "such as," or "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "polymer" indicates a large molecule comprised of repeating structural units ("-mers") typically connected by covalent chemical bonds.

While this invention is susceptible to embodiments in many different forms, there are shown in the drawings, which will herein be described in detail, several specific embodiments with the understanding that the present disclosure is to be considered as an exemplification of the principals of the invention and is not intended to limit the invention to the illustrated embodiments.

ABBREVIATIONS

ARC—anti-reflective coating.
BBB—blood brain barrier.
BMBC—brain metastasis from a primary breast cancer.
BLM—bilipid membrane.
bps—base pairs.
cDNA—complementary DNA.
CDC—clock distribution circuit.
CK—clock signal.
CMOS—complementary metal-oxide-semiconductor.
DAC—Disease associated cell.
DNA—deoxyribonucleic acid.
EEBI—environmental-electronic-binding-interface.
EEBITA—EEBI targeting agents
EEBIG—EEBI gaskets.
EEBIL—EEBI linkers.
EEBIP—EEBI pad.
ER—estrogen receptor.
FAB—antigen binding fragment.
GI—gastro-intestinal.
HER2—human epidermal growth factor receptor 2.
IC—integrated circuitry.
kDa—kilodalton.
MNSDED—micro/nano-sensing-deciding-effecting-devices.
nm—nanometer.
PEG—poly-ethylene glycol.
PEI—polyethylenimine.
PR—photoresist.
RF—radiofrequency.
RFEHC—radiofrequency energy harvesting circuit.
RNA—ribonucleic acid.
SDE—sensing-deciding-effecting.
SED—standard spin-expose-develop.
siRNA—small interfering RNA.
ssDNA—single stranded DNA.
UV/Vis—ultraviolet/visible
μm—micrometer.

MNSDED Overview

The term "micro-nano-sensing-deciding-effecting-device" ("MNSDED") as used herein indicates a composite nanorobot structure of microscale-to-nanoscale dimensions. The portion of the MNSDED contacting an environment external to the MNSDED is generally identified as the surface of the MNSDED. A typical MNSDED would be ovoid-to-cuboid, although different morphologies and deviations from this basic geometry are possible and may be necessary depending on the particular requirements of the MNSDED. A MNSDED may have a major axis length typically in the range of from about 100 nm to about 500 μm. Though generally ovoid-to-cuboid, the embodiments of MNSDEDs described herein will be described by a spherical approximation having a diameter from about 100 nm to about 500 μm. Factors driving these size scales and dimensions include, but are not limited to, size limitations dictated by in-vivo mobility through tissues, target DAC sizes, and circuit functionality requirements, among other factors. The specific MNSDED diameter will depend at least in part on the MNSDED composition and on the functional design that enables the MNSDED to serve its intended use. For example, MNSDEDs to be used with limited functional ability (e.g. containing few functional components as described herein) may have a diameter of about 1 μm or less, and the MNSDEDs employed with extensive functional ability (e.g. containing multiple functional components as described herein) may have a diameter from about 1 μm to about 500 μm.

More specifically, a MNSDED is comprised of transistors and associated integrated circuitry ("IC") contained within a "housing" of dielectric or any non-conductive material, which may be coated with one or more biocompatible surface coatings or protective agents and one or more targeting ligands. The one or more biocompatible surface coatings or protective agents may include, but are not limited to, poly-ethylene glycol ("PEG"). The one or more targeting ligands may include, but are not limited to, antibodies. The MNSDED may include targeting ligands and electrically conductive linkers that enable sensing of a chemical or biological environment, electrically conductive surface components that enable the intake and conversion of the information sensed from the environment into an electrical signal, IC components that enable or process logical decisions as to an intended action based on the sensed environment, and components that enable effecting one or more appropriate actions based on the decision.

MNSDED Sizes:

In some embodiments, the MNSDED may be sufficiently small to be able to conduct relevant cellular-MNSDED therapeutic interactions. For example, a *Staphylococcus aureus* cell has a diameter of ~1 µm, so a relevant therapeutically-designed MNSDED would correspondingly be on a scale of 1 µm diameter. Consequently, a MNSDED may contain fully functional ICs that have a standard Semiconductor Industry Association ("SA") node that is no more than 10 nm, which is a scale which enables a sufficient number of associated sensing-deciding-effecting ("SDE")-transistor-based components on a diagnostically or therapeutically effective MNSDED. These ICs are designed and arranged to carry out multiple functions including supporting a radiofrequency ("RF")-induced power source, employing a differential amplifier for binding-signal detection, applying input/output ("O") logic that processes specific bar-code type patterns of ligand binding, and activating an effector mechanism, among others.

The system, apparatus, and methods disclosed herein may rely, in part, on cellular transport of the described MNSDEDs to allow both cellular internalization and sub-cellular localization of the MNSDEDs as well transport through diffusion or convection through various tissues. In some cases, the described system, apparatus and methods may make use of some form of endosome-or-phagosome-facilitated transport through the targeted cell. This and other practical aspects, for example, avidity, may cause size to be a factor in designing a MNSDED for therapeutic use. For example, the avidity of MSNDEDs may be tuned such that they are able to irreversibly associate (bind) with DACs, but reversibly associate (bind and release) with healthy cells. Some MNSDED embodiments may be designed to be administered through stereotactic injection into dense tissues (e.g. some solid tumors, brain parenchyma), and the MNSDED size may be tuned so that it may transport through those tissues with relatively high diffusivity (e.g. employing a diameter of 500 nm or less). In other embodiments, for example, the MNSDED may be designed to be orally administered and targeted to eliminating *Helicobacter pylori* infection of the gastric mucosa, and the MNSDED size may be tuned so that it can maximally bind to, and employ an effector mechanism against this bacterium on a size diameter scale of about 1 to 4 µm, without concern for transport through dense tissues. In other embodiments, for example, the MNSDED may be injected intravenously, and it may be designed to flow freely through small vessels, including capillaries, necessitating that the MNSDED size be on a size diameter scale of no more than 4 to 8 µm. In other embodiments, for example, the MNSDED may be designed to bind to select neurons in nervous tissue in order to modulate neuronal activity through an electrical-based effector mechanism, and the MNSDED size may be tuned to be on the same size diameter scale of the neuronal body at about 4 to 100 µm. In yet other embodiments, for example, the MNSDED may be designed to bind and eliminate adipocytes after direct administration into adipose tissue, and the MNSDED size may be tuned to be on the same size diameter scale of the adipocytes at about 100-500 µm.

MNSDED Zeta Potentials:

The system, apparatus, and methods described herein may rely, at least in part, on diffusion or convection of the described MNSDEDs through various tissues, for example, blood plasma and whole blood. In designing MNSDEDs to specifically interact with pathogenic entities (including DACs and viruses), it is useful to take into consideration aspects of the MNSDEDs that may inhibit non-specific interactions of the MNSDEDs with interstitial fluid components, plasma components, whole blood components, and bulk components of tissues to which the MNSDEDs are administered. One such property is the zeta potential of the MNSDED. Accordingly, the system, apparatus and methods described may be carried out using a targeted MNSDED that includes a MNSDED core, as described herein, that is conjugated to any one of the targeting agents described herein, and further conjugated to biocompatible surface protective coatings described herein, where the zeta potential of the MNSDED is slightly negative to near neutral. Zeta potentials of the described MNSDEDs can vary depending on the materials used to manufacture the MNSDED core, the linker used, the targeting agent, and the biocompatible surface protective coating or protective agent (all described herein). In most cases, the zeta potential of the targeted MNSDED will fall in the negative range. To reduce immunogenic potential and reduce potential for biofouling, zeta potentials of the MNSDEDs for use with the system, apparatus, and methods described herein may range from about 0 mV to about −20 mV. Additional desirable properties of the MNSDED, including but not limited to surface charges and steric stabilization, may also vary in view of the specific application of interest.

MNSDED Detection Methods:

MNSDED dimensions and properties may be detected or measured by techniques known in the art. Exemplary techniques to detect particle dimensions include, but are not limited to, dynamic light scattering ("DLS") and nanoparticle tracking analysis ("NTA") and a variety of microscopies including transmission electron microscopy ("TEM"), scanning electron microscopy ("SEM"), and atomic force microscopy ("AFM"). Exemplary techniques to detect particle morphology include, but are not limited to, TEM and AFM. Exemplary techniques to detect surface charges of the MNSDED include, but are not limited to, the zeta potential method and NTA. Additional techniques suitable to detect other chemical properties include $^1H$, $^{13}C$, and other isotope-enabled nuclear magnetic resonance ("NMR"), UV/Vis and infrared/Raman spectroscopies, fluorescence spectroscopy and microscopy (when the MNSDED is used in combination with fluorescent labels, or when the MNSDED transistors are activated and emit infrared light), and additional techniques that would be apparent to one of ordinary skill.

MNSDED Modes of Administration:

The MNSDEDs described herein may be administered orally in any acceptable dosage forms, for example, capsules, tablets, aqueous suspensions, solutions or the like. The MNSDEDs may also be administered parenterally including but not limited to subcutaneous, cutaneous, intranasal, intravenous, intraarterial, intramuscular, intra-articular, intrasynovial, intrasternal, intraocular, intrathecal, intracerebral, intravaginal, intraurethral, intrarectal, intrapulmonary, and intracranial injection, or by stereotactic-assisted or infusion techniques. Alternatively, the MNSDEDs may be administered directly into a tissue of interest, for example, by direct injection into adipose tissue, or, for example, by intravenous or intraperitoneal injection, or, for example, by injection to the gastro-intestinal ("GI") system through J-tubes or G-J tubes.

MNSDED Use Cases:

Some embodiments may be designed for specific modes of administration with corresponding target diseases including, but not limited to, oral administration—for treatment of GI associated pathology including GI associated cancer (esophageal carcinoma, adenocarcinoma of colon etc.), GI associated infection (for example, *Clostridium difficile* or *Helicobacter pylori*), and for systemic treatment of disease where the MNSDED is designed to cross the blood-intestinal barrier; J-tubes, G-J tubes, or any other administration requiring GI procedures—for treatment of both upper GI tract disorders upon dysphagia or other per os ("PO") difficulties and for treatment of lower GI tract associated diseases where it is advantageous to prevent MNSDED exposure to the upper GI tract (e.g. acidity concerns); intravenous, intraarterial, intracardiac, intravascular administration—for systemic treatment of multiple pathologies (specifically useful for treating hematologic cancers and sepsis); intraperitoneal ("IP") administration—for treatment of IP associated pathologies, including endometriosis, peritonitis, etc.; sub cutaneous administration—for the treatment of localized pathologies such as dermatologic carcinomas "melanoma" and for regionally targeted concentration of therapy into regional lymph for treatment of pathologies including lymphomas, breast cancer, autoimmune disease, and any other lymph-associated pathology; intra muscular administration—for musculoskeletal associated disease (e.g. sarcomas, gene therapy for muscular dystrophy); intraocular administration—for retinomas, or reduction of inflammatory response in other ophthalmologic disease—e.g. retinitis pigmentosa; intrathecal or intracerebral administration—for the treatment of central nervous system related pathologies, including gliomas and glioblastomas, reduction of central nervous system ("CNS") associated inflammation with other diseases (e.g. multiple sclerosis, lysosomal storage diseases including Batten Disease), and direct treatment of neurodegenerative diseases including Alzheimer's, Parkinson's, and Huntington's Diseases; intravaginal and intraurethral administration—for the treatment of sexually transmitted diseases, and gynecologic infectious diseases and cancers (cervical cancer, vaginal cancer, bladder cancer etc.), and for the for the treatment of urinary tract infections; intrarectal administration—for the treatment of lower GI and rectal-associated disease, including *Clostridium difficile* infection, Crohn's Disease and other inflammatory bowel diseases, and lower GI cancers, etc.; intrapulmonary administration—for the treatment of pulmonary pathologies including pulmonary cancers, restrictive lung disease and infectious diseases; intranasal administration—for targeted CNS treatment and ear, nose, and throat ("ENT") associated pathologies; localized administration (e.g. stereotactic injection into solid tumors for associated treatment, or direct injection into adipose tissue for targeted reduction of adipocytes for the treatment of obesity).

MNSDEDs are not limited to intracorporeal use cases and may be designed for any use case that utilizes chemical or biological environmental sensing. MNSDEDs may be further utilized for any purpose that employs logic-based decision making and the subsequent effector mechanism execution, system, apparatus, and methods for which are described here within.

MNSDED Structures and Methods of Operation

The following will summarize the main subsystems and components of the MNSDED, the associated circuitry and non-circuitry related components, the composition of the components of the MNSDED, and a description of the methods in which these MNSDEDs may be synthesized, organized, specialized, administered, and used. Any examples that are described herein are not intended to limit the scope of the system, apparatus, method or composition, but rather to provide clarification of a broader concept through specific description.

A typical MNSDED may be divided into a number of subsystems, which interoperate with each other to achieve a desired therapeutic, imaging or chemical sensing outcome. Each of the subsystems described below may be modified with specific design features to achieve a desired end use case or outcome. In general, the MNSDED may be comprised of at least the following subsystems: (1) the sensing subsystem; (2) the deciding subsystem; (3) the effecting subsystem; and (4) an associated power supply and signaling subsystem.

MNSDED Sensing Subsystem

The MNSDED sensing subsystem may be comprised of at least the following components and materials: (1) environmental-electronic-binding-interface targeting agent; (2) environmental-electronic-binding-interface pad; (3) environmental-electronic-binding-interface linker; (4) environmental-electronic-binding-interface molecular trim pair; (5) environmental-electronic-binding-interface gasket; and (6) biocompatible surface-protective coating.

Environmental-electronic-binding-interface ("EFBI") is a term that will be employed herein to describe the assembly of components and materials of the MNSDED that are associating with, interacting with, and sensing the surrounding environment and, in some embodiments, transferring chemical or biochemical information from this environment to other components of the MNSDED by converting this chemical or biochemical information into an electrical signal that the MNSDED electronic components may process. The term "sensing" refers to the specific process of the MNSDED associating with the environment through specific binding interactions and converting chemical and biological information into electrical information that is propagated into the MNSDED circuitry.

EEBI Targeting Agent ("EEBITA") (also described herein as a "target binding molecule", "targeting ligand", "ligand", "targeting agent", or "capture agent") may serve as an interface that binds the MNSDED specifically to any virus or cell type of interest (e.g. DACs), or to a specific chemical or biological entity of interest in the environment, the latter or which may not be associated with a cell. The term "target" as used herein indicates any chemical entity or any biochemical entity including any biological system of interest including organs, tissues, cells or any portion thereof and may include in vitro or in vivo biological systems or any portion thereof. The term "target" as used herein may also indicate a non-biological entity of interest, such as a molecule or chemical that is not derived from a natural source. The term "EEBITA" or "target binding molecule" or "targeting agent" or "ligand" or "targeting ligand" or "capture agent" as used in the present disclosure indicates any molecule that can be presented on the surface of a MNSDED for the purpose of engaging a specific target, and, in particular, specific cellular or chemical recognition, for example, by enabling attachment of the MNSDED itself to a specific DAC receptor. Examples of suitable EEBITAs include, but are not limited to, vitamins (e.g. folic acid), proteins (e.g. transferrin, and monoclonal antibodies), monosaccharides (e.g. galactose), peptides, oligomers, small molecules, amino acid-based biomolecules (e.g. DNA, cDNA, RNA) and polysaccharides. In particular, EEBITAs may be antibodies against certain surface cell receptors (for example, CD19 that is implicated in non-Hodgkins Lymphoma). The term "antibody" includes reference to an immunoglobulin molecule that is reactive with a particular antigen. The term also includes genetically engineered forms such as chimeric antibodies (e.g., humanized murine antibodies), heteroconjugate antibodies (e.g., bispecific antibodies) and recombinant single chain variable fragments ("scFv"), disulfide stabilized ("dsFv") Fv fragments, or pFv fragments. The term "antibody" also includes antigen binding forms of antibodies (e.g., Fab', F(ab')2, Fab, Fv, rIgG and others) that are known to those skilled in the art (see, for example, as disclosed in U.S. Pat. No. 7,081,518, which is hereby incorporated by reference in its entirety). An antibody immunologically reactive with, or "specific for," a particular antigen is a relative term. As provided in the Definitions herein, the term "attach," "attached" or "attachment" as used herein, refers to connecting or uniting by a chemical bond, link, or force in order to keep two or more components together. This encompasses either direct or indirect attachment, for example where a first compound is directly bound to a second compound, and the embodiments wherein one or more intermediate compounds are disposed between the first compound and the second compound. The interaction of the EEBITA with a predetermined chemical or biomolecular target will initiate a series of events to be described herein that will send an electric signal to the MNSDED with information that designates that a specific environmental-, chemical-, or biomolecular-EEBITA binding event has occurred.

The EEBITA may include a ligand that is specific to a particular chemical functional group, chemical bond, or combination of chemical functional groups, steric regions, or other chemically related entities where interactions may occur. The EEBITA may also include a ligand specific for a receptor expressed on a cancer cell, an autoimmune-associated cell, an infectious disease associated cell, or any other DAC. These receptors may be specific to membrane-associated receptors, receptors that are internalized, receptors that transcytose, receptors that are associated to lysosomal trafficking, or receptors that are associated with trafficking to any other subcellular compartment. For therapeutic applications, for example, EEBITAs that are associated with specific receptors may dictate the overall MNSDED design in terms of both integrated circuitry and therapeutic mechanism. For example, EEBITAs that target receptors that are associated with cancerous cells in solid tumors may be useful for MNSDEDs that have activated components in acidic environments. This may include acid-dissolvable membranes that release therapeutic agents from MNSDED drug-compartments that will be described in further detail herein.

Ideally, a targeted therapeutic will be capable of reaching multiple tissue targets in order to treat a broad range of diseases. For instance, it may be possible to target receptors that transcytose at the blood brain barrier ("BBB") in order for the MNSDED to cross this barrier. It may further be possible to take advantage of chemical changes experienced during receptor mediated transcytosis to increase accumulation of MNSDEDs within anatomically isolated organs. Disclosed herein are methods of delivering a MNSDED to such anatomically isolated and privileged areas (e.g. the brain, the retina, the testes, the prostate, etc.) of a subject that are partitioned from the circulation by a largely vascular barrier, by administering to the subject a MNSDED having a EEBITA intended for receptors that facilitate transport across such barriers. A variety of EEBITAs may serve to promote delivery of the disclosed MNSDED. Brain-specific therapeutic strategies may include the treatment of multiple sclerosis through elimination of disease-associated CD4 T cells or any other specific neuroinflammation mechanism, or the treatment of meningitis/encephalitis through elimination of bacterial DACs or viruses, or the treatment of primary or secondary brain cancers, for example, gliomas, glioblastomas, or secondary breast cancer.

To carry out the described methods it may be advantageous to control the number and types of EEBITAs that are attached to the described MNSDEDs. A MNSDED may contain as few as one EEBITA, and they may contain as many as can be accommodated by the physical space available on the surface of the MNSDED. The number and types of EEBITAs may be varied depending on the type of MNSDED being delivered, the targeted pathogenic entity, or a host of other factors. The number and types of EEBITAs may be varied to maximize the electronic signal transferred to the IC of the MNSDED while ensuring the MNSDED retains biocompatible characteristics (e.g. biocompatible zeta potential, minimized potential for immunogenicity, minimized potential for binding to unintended targets with corresponding maximized therapeutic effect and minimized off-target effects, etc.). The number and types of EEBITAs may be tuned so that the MNSDED irreversibly binds to pathogenic entities (including DACs and viruses) with small binding dissociation constants ($K_d$), and reversibly or transiently binds to healthy cells with large binding dissociation constants.

EEBI Pads ("EEBIP") are located on the surface of the MNSDED and comprised of materials that are electrically conductive, and whose surface may be chemically modified (as described herein). These materials may include but are not limited to metals (for example, gold, silver, copper, titanium, or other metallic materials known to those skilled in the art of microelectronics manufacturing) and semiconductive materials (e.g. silicon) that are doped sufficiently to become a conductive material, through methods known by those skilled in the art. These EEBIPs will be the direct physical and electrical connection on the surface of the MNSDED to the MNSDED integrated circuitry that will be described in further detail herein. The EEBIP itself may be of any dimension constrained by the size of the MNSDED surface and may be of elliptical or rectilinear shape with a critical dimension (e.g. diameter or major axis length) that is sufficiently large to accommodate the hydrodynamic radius of the associated EEBITA. For example, in some embodiments, the critical dimension of the EEBIP may be no less than about 10 nm in length, which is sufficient to accommodate an EEBITA that is an antibody with a hydrodynamic radius of about 10 nm. In other embodiments, the critical dimension of the EEBIP may be no less than about 30 nm in length, which is sufficient to accommodate two EEBITAs, both of which are antibodies, each having a hydrodynamic radius of about 10 nm, and each having a nominal amount of space permitting a spatial degree of freedom. Each EEBIP will be sufficiently large to contain or accommodate at least one EEBITA or targeting ligand, and the EEBIP size may be varied to be sufficiently large to contain or enable the utilization of as many EEBITAs as are practicable for the designated purpose of the MNSDED. The design of the EEBIP critical dimension will take into consideration the size of the associated EEBITA and linker. The EEBIP critical dimension may ideally be no more than about 10% larger than the hydrodynamic radius of the EEBITA, and often less. In embodiments where the linker has a larger hydrodynamic radius than the EEBITA, the EEBIP critical dimension may ideally be no more than about 10% larger than the hydrodynamic radius of the linker, and often less. The EEBIP will be designed to be as small as possible on the MNSDED surface to ensure that electronically conducted signal through the linker is above the electronic signal-to-noise ratio, where the signal is associated with a specific binding event of an EEBITA to its target, and the noise is associated with non-specific binding events and background electrochemical potential and thermal fluctuations.

The EEBITA may be bound directly to the EEBIP as is described in further detail in the "EEBI Linkers" section herein. There may be at least one EEBIP for each unique EEBITA, and there may be at least one EEBITA contained within or associated with each MNSDED, with up to as many EEBITAs as are needed in the functional design of the MNSDED and that can be sterically placed on the surface of the MNSDED. For example, one embodiment may be designed to target CD19 and CD71, and therefore this embodiment may contain an EEBIP with one unique EEBITA that is an antibody targeting CD19 and a second EEBIP with a second unique EEBITA that is an antibody targeting CD71, where there may be as many CD19-associated EEBIPs and CD71-associated EEBIPs that can practically fit on the surface of the MNSDED.

Once all EEBITAs have been attached to the EEBIP, a protectant small molecule (for example a methoxy-(n-alkyl)-thiol, or other molecule) may be attached to the remaining exposed areas of the EEBIP for the purposes of shielding against non-specific fouling by environmental molecules.

EEBI Linkers ("EEBILs") may serve to attach the EEBITA to the EEBIP and to carry any electron transfer or charge transfer to the EEBIP arising from an EEBITA specific-binding event. The EEBIL may be comprised of any combination of bio-conjugately or chemically linked small molecules, biomolecules, compounds, polymers, moieties, or other entities, and they may be designed to be as small as practicable (e.g. low '-mer' length in embodiments that use polymers as EEBILs) in order to minimize the attenuation of the charge transfer across the EEBIL and increase the ability of the EEBIL to elicit a voltage change at the EEBIP through charge transfer facilitated by the EEBIL when there is a specific EEBITA-to-target binding event.

The term "polymer" as used herein indicates a large molecule comprised of repeating structural units ("-mers") typically connected by covalent chemical bonds. A suitable polymer may be linear and/or branched, and it may take the form of a homopolymer or a co-polymer. If a co-polymer is used, the co-polymer may be a random co-polymer or a branched co-polymer. Exemplary polymers will be water-dispersible and in particular water-soluble polymers. For example, suitable polymers include, but are not limited to, polysaccharides, polyesters, polyamides, polyethers, polycarbonates, polyacrylates, etc. Ideally, the polymer will retain high stability under conditions seen in biologic environments (e.g. temperature of 37° C., pH ranging from 2 to 7.4) as well as under MNSDED fabrication conditions (e.g. temperatures ranging from 250° C. to 100° C., and other conditions as will be described further herein). For therapeutic and/or pharmaceutical uses and applications the polymer will ideally have a low toxicity and cytotoxicity profile. Suitable polymers include those having a molecular weight of about 10,000 Da and below.

Ideally, an EEBIL will be chosen that serves as a medium that may transfer electrons or a change in electric field (i.e. electrical binding information) over the EEBIL's entire length regardless of Debye shielding lengths and independent of solvent-associated double-layer capacitances. In physiological and biochemical environments where some MNSDEDs may be expected to function, Debye shielding, induced by high (physiologic) salt concentrations, is well accepted to be prohibitively attenuating to field-effects that would otherwise be experienced by an EEBIP when a specific binding event elicits an electric field change that would induce a voltage change in an EEBIP. Due to Debye shielding concerns under physiologic conditions, some embodiments may require a charge carrying EEBIL to overcome this Debye shielding barrier, which in many in vivo applications will render field effect modulation of electric potential at the EEBIP inutile. Charge carrying EEBIL molecules may be polymeric (e.g. polyethylenimine ("PEI") or conductive polymer polypyrrole) or biomolecules (e.g. DNA wires), or any other chemical or biological composition that can facilitate charge transfer or electron transfer. In this case, the length of the EEBIL may be tuned to balance the stability of the linker with the ability of the linker to transfer charge to or effect a local change in electric potential at the EEBIP. For instance, in some embodiments, the EEBIL will be comprised of DNA, and the size of the EEBIL will be dictated by the total number of DNA base pairs ("bps"). In this embodiment the total number of bps will be tuned to ensure there is sufficient binding strength between the complementary DNA strands (e.g. the annealing temperature ($T_{anneal}$) is at least greater than physiologic temperature of 37° C.), while ensuring that there are few enough base pairs to ensure that sufficient electrical conductivity is achieved to elicit a charge transfer to the EEBIP without significant attenuation of charge transfer that may occur entropically or through other mechanisms over large distances (for example, according to Slinker, typically DNA wires can carry electric current with fewer than 100 complementary bps across as much as 34 nm, with inverse relationship between electrical conductivity and total base pair number—doi: 10.1038/nchem.982). Ideally, in this embodiment, the length of the EEBIL will be dictated by the minimum number of bps to achieve the condition that ($T_{anneal} > T_{physiologic}$), with the constraint that the number of bps is sufficiently low to achieve an electrical signal that results in a reference-to-target EEBIP electric potential difference that is at least on the picovolt scale, as will be described further herein. $T_{anneal}$ is under additional constraint such that it must be less than any temperature that would denature, degrade, or otherwise damage the EEBITA (for example, many antibodies degrade at greater than 70° C., and many proteins denature at greater than 41° C.). Under these constraints, the EEBILs will be no more than about 10 nm in length (or about 30 bps) in some embodiments and will likely be less. Further under these constraints, the selection of base pair sequence will be optimized so that $T_{anneal}$ that will enable the lowest number of bps, and the shortest EEBILs possible.

The EEBIL attachment to an EEBIP may be facilitated through a functional handle that is placed onto the surface of the EEBIP. This functional handle may be of any chemical functional group that will be described herein and will ideally be of small length (e.g. a small molecule of less than 400 Da and of chemical length of no more than about 2 nm) and specific chemical functionality to facilitate a distinct conjugate reaction as will be described herein. An example functional handle may be achieved through reacting a thio-(n-alkyl)-amine with the metallic EEBIP surface to create a metal-thiol dative bond that will facilitate a primary amine functional handle near the surface of a metal EEBIP. This primary amine functional handle can subsequently undergo further conjugate chemistry that enables the binding of a larger EEBIL molecule (e.g. a complementarily functionalized DNA wire). For example, in some embodiments, the aforementioned EEBIP-associated-primary amine functional handle can react with an N-hydroxyl-succinimide-ssDNA molecule (or other nucleobase binding molecule), thus forming an amide covalent bond between the cDNA molecule and the EEBIP. Further, as needed, a functional handle may be placed on the EEBIL itself, or the EEBITA, in order to facilitate the binding of the EEBIL to the EEBIP, or the EEBIL to the EEBITA. For example, an EEBITA that is a protein may be functionalized with sulfhydryls by reacting the primary amines of the protein's lysine groups with N-succinimidyl 3-(2-pyridyldithio) propionate (SPDP), followed by reductive treatment with dithiothreitol (DTT). The resulting sulfhydryl groups on the proteins may the serve as functional handles for reaction with maleimide-ssDNA to form ssDNA-protein (or EEBIL-EEBITA).

A variety of functional handles may facilitate linkage of the EEBILs to the EEBIPs and the EEBILs to the EEBITAs, and these functional handles may be used to carry out the disclosed methods. In some of the embodiments, the functional handle may include one or more of the following, alone or in combination: an amine, a thiol, a carboxylate, a hydroxyl, an aldehyde, a ketone, a diazonium, an aryl azide, a halogenated aryl azide, a benzophenone, an anthraquinone, an alkyne, a biotin, a polypeptide or any other chemically active group. Those skilled in the art will understand that other functional handles could be employed in a similar manner to cause association between an EEBITA and an EEBIP. These functional handles may be chemically bound to the EEBIPs through associated chemical reactions directed by photolithographic patterning as will be described in further detail herein. Ideally, the functional handles will be as small as practicable, and in applications where MNS-DEDs are employed in physiologic environments, they will often less than about 2 nm in length to overcome Debye shielding for charge transfer from the charge carrying polymer, across the functional handle, and to the EEBIP. In most applications the functional handles may be no more than about 1 nm in length. This functional handle may be available for conjugation reactions with chemical moieties that are able to chemically interact with high specificity and selectivity to that functional handle and facilitate the binding of EEBIP to the EEBIL, or the EEBIL to the EEBITA. For example, amine functional handles may react with isothiocyanates, isocyanates, acyl azides, NHS esters, sulfonyl chlorides, aldehydes, glyoxals, expoxides, oxiranes, carbonates, arylating agents, imidoesters, carbodiimides, anhydrides, fluorophenyl esters, hydroxymethyl phosphine derivatives, and guanidinates. Thiols may react with haloacetyl derivatives, alkyl halide derivatives, maleimides, aziridines, acroloyl derivatives, arylating agents, thio-disulfide exchange agents (pyriyl disulfides, TNB-thiol), vinylsulfone derivatives, metal-thiol dative bonding, and cisplatin derivatives. Carboxylates may react with diazoalkanes, diazoacetyl compounds, carbonyldiimidazole, and carbodiimides. Hydroxyls may react with epoxides, oxiranes, carbonyldiimidazole, N,N'-Disuccinimidyl carbonate, N-hydroxysuccinimidyl chloroformate, periodates, alkyl halogens, and isocyanates. Aldehydes and ketones may react with hydrazine derivatives or may undergo Schiff Base formation, reductive amination, or Mannich Condensation. Diazoniums may react with activated hydrogen sites on aromatic rings. Aryl azides and halogenated aryl azides may react with N—H and C—H associated active sites. Benzophenones may react with C—H active sites. Anthraquinones may react with specific radical pair reactions. Alkynes may react with Azido-functional groups. Biotin may react with avidin.

Based on the foregoing disclosure, those skilled in the art will understand that a variety of functional handle molecules may be used with the described EEBIPs, EEBILs, and EEBITAs in order to enable the association of a specific EEBITA to corresponding EEBIP. Such alternatives, as would be apparent to one of ordinary skill in view of the present disclosure, are considered to be within the scope of this disclosure. Furthermore, functional handles described as associated with the EEBIPs may be associated with the EEBITAs, and vice versa.

EEBILs may themselves be capture agents, for example oligonucleotide stem-loop receptors, which undergo conformational changes upon binding of a target, and which juxtapose phosphate backbone charges to the EEBIP to less than the Debye length (<1 nm), can create a specific voltage change within the EEBIP (as described in Nakatsuka, N. et al. (2018) Aptamer-field-effect transistors overcome Debye length limitations for small-molecule sensing. Science 362, 319-324, which is hereby incorporated by reference in its entirety).

EEBI Molecular Trim Pair ("EEBIMTP"), is the term that will be employed to describe the whole assembly of a reference molecule (described herein) coupled to a reference-associated EEBIP ("reference EEBIP") through the same linker and functional handle-assembly (same EEBIL assembly) that is used to couple an EEBITA to a target-associated EEBIP ("target EEBIP"), the voltage of the reference EEBIP being compared to the voltage of a target EEBIP through a differential amplifier. The EEBIMTP may serve as a voltage and capacitance comparator in the case that a non-specific binding event occurs on the target EEBIP, the voltage and capacitance difference being determined through a differential amplifier as is described further herein. These EEBIMTPs may ensure that, upon non-specific binding of the target EEBIP, there will be a negligible voltage difference (enabled through voltage comparison by the differential amplifier) between the target EEBIP and the corresponding reference EEBIP. This EEBIMTP may therefore ensure that the latch (described herein) will not trigger on non-specific interaction events associated with the target EEBIP, e.g., a false positive. The EEBIMTP may be calibrated by identifying and binding a "reference" molecule or biomolecule to the reference EEBIP. This "reference" molecule or biomolecule may be tuned or selected so that when it interacts non-specifically with the environment (including non-specific cellular interactions), it will effect a near equivalent voltage change in the reference EEBIP as will be created in the target EEBIP when the EEBITA engages in non-specific interactions. These EEBIMTPs may be configured and designed based on the particular application of the MNSDED, and may be configured and designed through experimental development, with configuration and design of the EEBIMTP further informed by the particular environment in which the MNSDED is to be administered. For example, in some embodiments, if the MNSDED is to be administered intravenously in humans, the EEBIMTP "reference" molecule could potentially be based on an albumin molecule (to mimic the immediately surrounding environment of the MNSDED), or in the case that an antibody is the MNSDED targeting ligand, the EEBIMTP "reference" molecule may be based on an antibody specific to an antigen not found in humans. The "reference" molecules or biomolecules to be conjugated to the reference EEBIP may include, but are not limited to, polymers (e.g. PEG, PEI etc.), glycoproteins, proteins (e.g. antibodies, antibody fragments, albumin), nucleic acids, lipids (e.g. palmitate), small molecules, and any other molecule or biomolecule that accomplishes the purpose and function of the EEBIMTP.

In some embodiments, there will be at least one reference EEBIP for every target EEBIP. The reference EEBIP(s) corresponding to the target EEBIP may be located adjacent to the associated, target EEBIP, and may be coupled to the target EEBIP through a differential amplifier that is described in further detail herein. In some embodiments there may be two or more reference EEBIPs for every target EEBIP. In the case that there is more than one reference EEBIP associated with a target EEBIP, those reference EEBIPs may be coupled to each other through a differential amplifier (one differential amplifier between each pair of reference EEBIPs), in addition to each reference EEBIP being coupled to the target EEBIP through additional dedicated differential amplifiers. In such embodiments these reference EEBIPs will serve to minimize or possibly to eliminate any false-positive-identification events of the target EEBIP, by comparing the voltage difference between the reference EEBIPs to the voltage difference between the reference EEBIPs and the target EEBIP. By way of illustration, for example, in the case that there is less than a few percent difference between these reference EEBIPs and target EEBIP voltage differences, the latch (described herein) will not be triggered, and the MNSDED effector subsystem state will remain unchanged.

Sense amplifiers will be incorporated into the integrated circuitry in order to amplify the voltage difference between any two EEBIPs (e.g. the voltage difference between a target EEBIP and a reference EEBIP, or the voltage difference between two reference EEBIPs). When an EEBITA on an EEBIP is attached to its target (e.g. CD19 specific IgG attached to CD19 on a lymphoma cell), there will be a change in the electric field distribution around the target EEBIP with associated electrical signal conductance through its corresponding EEBIL, which differs from the field distribution around the reference EEBIP and associated electrical signal conductance through the associated EEBIL with its non-specific background voltage. The resulting difference in target-to-reference EEBIP voltages may be detected and amplified from initial voltage differences and converted to a complementary metal-oxide-semiconductor ("CMOS") logic level for use by the MNSDED control circuitry. The sense amplifier output may be subject to further signal conditioning (e.g., amplification, filtering) and is then latched into a storage circuit. Regenerative sense amplifiers incorporating clocked cross-coupled pairs with precharge, measure, and latch phases may be employed to boost the small voltage differences between the reference and target EEBIP to CMOS logic levels. These clocked sense amplifiers will output multiple measurements based on one or more clock frequencies. If these varieties of sense amplifiers are employed, a threshold number of "positive" measurements per time interval may be counted by a counting/thresholding circuit that triggers downstream logic upon counting a predetermined number of "binding events", or multiple measurements of the same binding event. The counting circuit may then send a logical signal to the decision circuitry. This data or logical signal constitutes an input to a decision whether an EEBITA has bound to its specific target and becomes an input to the MNSDED control logic circuit.

EEBI Gaskets ("EEBIG") will serve to reinforce the barrier created by cell-surface associated glycocalyx/biomolecules and MNSDED associated surface protectant (e.g., PEG). This gasket may assist in the isolation of each target EEBIP from the surrounding environment when that target EEBIP's associated EEBITA has bound to its specific target. This may assist in buffering the ion concentration near the EEBITA-target binding site, thus decreasing/stabilizing the Debye shielding length, and increasing/stabilizing the capacitive (field effect) sensitivity of the EEBIP to a target-specific binding event (through field effect charge transfer through non-conductive components of the EEBIL, such as the functional handle that in some embodiments may couple the EEBIL to the EEBIP, and in some embodiments the moiety that couples the EEBIL to the EEBITA). This EEBIG may be a barrier around the circumference of the EEBIP that may be constructed of any molecule including, without limitation, polymers, lipids, proteins, oligomers, nucleic acids, or small molecules. These molecules may be specifically positioned around the EEBIP using the bio-compatible lithographic techniques described further herein. The molecules and associated linkers to the MNSDEDs may be designed so that they are sufficiently longer than the bio-compatible surface-protective coating layer, such that there is a robust seal, but not excessively longer than the biocompatible surface-protective coating layer, to permit diffusion of cell associated receptors toward the targeting ligand through a fluid-mosaic diffusive process. For example, in one embodiment, the molecules and associated linkers of the EEBIG to the MNSDED may be not less than about 10 nm but not longer than about 20 nm in order to exhibit the aforementioned sealing and diffusion characteristics. Molecules may be tuned to be "ion" sponges and contain molecular structures that effect as ion sponges (e.g. 1,8-bis (dimethylamino)-naphthalene, amongst others known to those skilled in the art), that may additionally reduce the ionic strength of the environment within the EEBIG itself. Molecules may be tuned to be hydrophobic to repel any aqueous-associated or hydrophilic entities, that may also reduce ionic strength of the environment within the EEBIG. This may also significantly decrease Debye shielding and increase the capacitive and field effect sensitivity of the EEBIPs.

Biocompatible Surface-Protective Coating:

A protective coating comprising any molecule (including, without limitation, biomolecules, lipids, constituents that typically make up vesicles, microsomes, or biologic membranes (e.g. red blood cell mimetic vesicles), and polymers such as PEG, PEI, and others) may be added to the surface of the MNSDED to ensure the molecule is biocompatible, non-immunogenic, and stable in physiologic solutions. Ideally, this protective coating will be thin enough to ensure the targeting ligand is not masked (e.g. 500 Da to 2 kDa), but will be large enough (e.g. 2 kDa to 10 kDa) to ensure adequate protection of the MNSDED from high solute concentration of physiologic solutions that are known to reduce Leonard-Jones potentials between individual MNSDEDs and allow for Van der Waals interactions between surfaces that may cause MNSDED aggregation and biofouling. This protective layer may additionally aid any field effect produced by the EEBITA-target interaction on the EEBIP, that may increase the charge transfer, electron transfer, or field effect transfer of electric potential in the MNSDED that is produced by specific binding of an EEBITA to a target receptor. An EEBIP field effect may be aided through increasing the Debye length by reducing Debye shielding through the addition of this biocompatible surface-protective coating immediately adjacent to the EEBIPs that may reduce the effective solute concentration in the vicinity of the EEBIP or further inhibit ionic entities from penetrating the EEBIG.

MNSDED Deciding Subsystem

The MNSDED deciding subsystem may be comprised of at least the following components and materials: (1) differential amplifier/comparator/latch circuitry that facilitates the detection of the initial binding of an EEBITA to a target, and (2) CMOS logic circuitry to turn the binding pattern into a logical decision to employ an effect or not to employ an effect on the bound cell.

Decision Logic Circuitry may be employed within the MNSDED to facilitate logical processing of combinatoric states, for instance when a single or group of distinct EEBITAs have bound (or not bound) their respective targets. The term "bar code type recognition" as used herein refers to a logic-based decision made by the MNSDED integrated circuitry that one or more EEBITAs have bound (or not bound) their respective targets, and further to initiate an effector mechanism based on a predefined combination of triggered (and un-triggered in some cases) latches that are specific to an ensemble of EEBITA binding events (e.g. for positive feedback) and possibly the lack of EEBITA binding events (for negative feedback control).

These decisions to activate the effecting subsystem may be facilitated through logic circuits that will serve as the control component that will dictate an output response for each bound-or-unbound EEBIP pair (target and reference EEBIP pair) or bound-or-unbound EEBIP grouping (target EEBIP and its associated one or more reference EEBIPs). The logic circuits (examples described herein) may satisfy the condition of Boolean functional completeness if necessary for the MNSDED design, and may be comprised of any combination of logic gates, (e.g. a combination of CMOS logic gates that can enable any Boolean function), and the final logic circuit design may be dictated by the MNSDED application decisional requirements. These logic circuits may take data derived from each EEBIP pair or grouping (i.e., a target EEBIP and its associated one or more reference EEBIPs) and combine all of these signals in appropriate logic/decision circuits to determine if the MNSDED should activate the effecting subsystem. Logic circuits for implementing AND, OR, NOT Boolean logic are well-known in the art, as is the practice of combining them into more complex logical decision making "logic blocks" to determine if a data pattern matches a decision criterion or multiple decision criteria.

For a therapeutic indication, for example, the deciding subsystem may be designed so that an EEBITA binding event will contribute through "AND" or "OR" circuitry or logic to a "on" or "therapeutically active state" in which the therapeutic effecting subsystem circuitry, described below, is activated. The logic circuit may also be designed so that EEBITA binding to a self-antigen or "safety disarm antigen" may be associated with a "NOT" gate (or equivalent circuitry to a "NOT" gate) and may effectively deactivate the therapeutic mechanism circuitry. With as many unique EEBITAs as will fit on the MNSDED surface (constrained by the size of the MNSDED and the size of the target), there is capacity for the MNSDED to effectively sense that it is bound uniquely to a DAC through bar-code type recognition, with both positive (disease associated) and negative (non-disease associated) inputs.

MNSDED Effecting Subsystem

The MNSDED effecting subsystem may be comprised of at least one or more of the following components and materials: (1) electroporation/electroshock nano-needles; and/or (2) targeted drug/imaging agent delivery components.

Electroporation/Electroshock Needles may be coupled with voltage amplifier circuits that will increase the voltage generated through the radiofrequency energy harvesting circuitry (described further herein) so that the MNSDED is capable of electroshocking or electroporating a bound DAC. The electroshock or electroporation action may be conducted through a series of no less than two nano-needles—one serving as the anode needle, and the second serving as the cathode needle (or ground). These nano-needles may protrude from the surface of the MNSDED, and they may be placed geographically on the MNSDED surface in a location that is as close as practicable to the EEBIPs, in order to allow for target EEBIPs and their associated reference EEBIPs to be in as close proximity as practicable to the nano-needles, also in order to ensure that the nano-needles are in as close proximity to the DAC bilipid membrane ("BLM") as practicable while minimizing the potential for the nano-needles to ablate or porate adjacent healthy cells to the MNSDED. The nano-needle pair location on the surface of the MNSDED may be far enough from the EEBIPs in order to decrease the electric field and local joule heating associated with current between the nano-needles that may cause the EEBITA(s) to dissociate from the target or damage the EEBITA(s) and EEBIMTPs themselves. Ideally, the nanoneedles will generally be no less than about 100 nm from the nearest EEBIP, though the exact distance of the nano-needles to the nearest EEBIP will be dictated by the functional MNSDED design and the overall MNSDED size and the total area that is available to accommodate all EEBIPs, nano-needles, and other MNSDED surface-associated components that are described herein. The nano-needles may be spaced so that their bases are separated by a distance that is sufficient to prevent electrical shorting between the bases, this distance being dictated by the optical proximity correction and etching profile limitations associated with the fabrication methods that are further described herein. In one embodiment, for example, the edge of one nano-needle base edge will be no less than about 10 nm from the edge of a second nano-needle base edge.

These nano-needles may be designed to penetrate the BLM when the MNSDED is attached to the cell of interest through specific EEBITA binding. These nano-needles may protrude through the biocompatible surface protective coating layer of the MNSDED at a length sufficient to ensure the needles penetrate through the DAC BLM, after which they may produce an electric field of sufficient strength to porate or ablate (break down) the BLM when specifically bound to a DAC. Furthermore, in some embodiments, the nano-needles may be designed so they are not excessively long, to minimize the likelihood they will protrude through BLMs when the MNSDEDs are non-specifically and transiently associated with non-targeted cells through any non-specific (e.g. electrostatic) interactions. For example, in one embodiment, the nano-needles should be no less than about 10 nm and no more than about 500 nm in length. These nano-needles may be designed to contain bio-compatible protectant agents conjugated to the surface while leaving the tip of the needle exposed for optimal reduced immunogenicity and retained electrical conductivity, specifically leaving a free path for electrons to pass from the anode to the cathode (ground) when the MNSDED effector is activated. In yet other embodiments, the nano-needles may be designed so they do not penetrate the BLM when the MNSDED is bound to a DAC through an EEBITA or EEBITAs, while they still can produce an electric field of sufficient strength to ablate or porate the BLM.

The ideal nano-needle will have a high-aspect-ratio in nanoscale dimensions in order to facilitate nano-needle penetration of the BLM without damaging the attached cell when the MNSDED effector is not activated, which would be indicated for non-specific interactions with non-DACs. For example, the nano-needle may have a diameter less than about 100 nm and a length between about 100 nm and 1 μm. Ideally, the nano-needle is mechanically robust in aqueous environments and the surface of the nano-needle may be functionalized similar to the biocompatible surface protective coating as described above. See Yum, K., Wang, N., and Yu, M-F. (2010) Nanoneedle: A multifunctional tool for biological studies in living cells. Nanoscale 2, 363-372, which is hereby incorporated by reference in its entirety.

Upon activation by the deciding subsystem, a voltage sufficient for electroporation (transient poration of the DAC BLM) or ablation (i.e. large-scale structural breakdown of the BLM and associated irreversible membrane rupture) may be applied through the nano-needles. As described further herein, voltages sufficient for ablation will be employed in applications where pathogenic entities (such as DACs) are intended to be eliminated, while voltages sufficient for poration will be employed in embodiments where pathogenic entities are intended to be treated, imaged, detected, or modified by the introduction of a therapeutic or imaging agent into the pathogenic entity through the transient pores created in the BLM (See Teissie, J. and Tsong, T. Y. (1981) Electric field induced transient pores in phospholipid bilayer vesicles. *Biochemistry* 20, 1548-1554, which is hereby incorporated by reference in its entirety). In one embodiment that is intended for irreversible membrane breakdown, a voltage will be applied of no less than about 80 mV and as much as about 5V (expecting irreversible membrane breakdown at 1V to 5 V), and this voltage will be applied for no less than about 1 millisecond and as much as several minutes. In an embodiment that is intended for electroporation only, less than about 1 V will be applied for a reduced time that is appropriate for poration or reversible membrane disruption (e.g. may be less than about 80 mV). Such electroporation may be coupled with release of small molecule (e.g., L-DOPA) or large molecule (e.g., siRNA, CRISPR/CAS9), or therapeutic or imaging agents that may facilitate rapid entry of these entities into only targeted cells. This delivery is described further in detail herein.

These nano-needles may be fabricated from any of the materials commonly known to those skilled in the art of microelectronic manufacturing, including but not limited to silicon, polysilicon, doped polysilicon, metal (e.g. gold, copper, titanium), hydrogel, polymer, sugars, and carbon nanotubes. Nano-needles may be fabricated through growth or deposition of material (e.g. silicon depositing on the MNSDED surface) followed by appropriate doping to create a conductive material, followed by lithographic printing of the area where the nano-needle is to reside, and followed by an etch process that will etch away all material that leaves the nano-needle as a surface feature on the MNSDED. The etch process may be tuned such that the nano-needle will be confined within the dimensions described above and such that it will be of a high aspect ratio with a reasonably pointed tip (e.g. about a 100 nm base tapered up to a <10 nm tip). The sharper the nanoneedle tip, the larger the voltage gradient at the tip will be, thus maximizing the electroablative and electroporative capacity of the nanoneedle. Nano-needles may be similarly fabricated from metal (e.g. copper, gold, aluminum, titanium), or polysilicon-based nano-needles may be coated with gold or other conductive thin film (e.g. TiN) that may reduce potential immunogenicities. Metal nano-needles may be created by any of the following techniques, including without limitation (1) metal coating of a non-metal nano-needle (e.g. via atomic layer deposition ("ALD")), (2) metal filling within a lithographically printed pore or via, (3) lithographically assisted etching of a metal layer (e.g. reactive ion etching of Ti). The metals employed in these techniques may include, but are not limited to gold, silver, aluminum and its oxides, copper, tungsten, platinum, ruthenium, nickel, titanium, and titanium nitride. Other nano-needle fabrication techniques may be used as long as the resulting nano-needles have the structural and performance characteristics described herein. Ideally, this nano-needle creation should be completed prior to any lithographically-aided chemical or bio-conjugation to the EEBI as described herein.

Targeted Drug/Imaging Agent Delivery Components: The disclosed system, apparatus and method may be used to deliver one or more therapeutic and/or imaging agents to pathogenic entities (including DACs and viruses), by loading into one or more compartments or "reservoirs" of the described MNSDED a therapeutic agent or imaging agent prior to administration of the MNSDED to the subject. Following delivery of the loaded MNSDED, the EEBITA may facilitate association of the MNSDED to a target DAC, for example, a tumor cell. Following binding of the EEBITA to the target on the DAC, the MNSDED may decide through the aforementioned deciding subsystem logic circuitry, whether or not to activate the therapeutic or imaging agent delivery components. In the case the effecting subsystem is activated by the deciding subsystem, the effecting subsystem may release therapeutics or imaging agents which are contained within the reservoir through the apparatus and method described herein.

Each reservoir may be a compartment within the MSNDED that is sealed from the external environment by a barrier that is composed of a metallic or polymeric material, or a barrier that is composed of any other chemical or biologic material. This barrier may be opened, dissolved, or degraded (when decided by a logic circuit) in order to release a therapeutic or imaging agent through any barrier-removal mechanism that is appropriately corresponding to the barrier material itself, and that may include, but is not limited to, pH catalyzed chemical removal, electric field or electric current-assisted removal, or thermoelectric-based temperature-assisted removal.

For example, in some embodiments, the barrier may be composed of a thermo-responsive material (e.g. poly(N-isopropyl-acrylamide), PNIPAM) that is stable in physiologic temperatures, but that may be dissolved upon heating to its melting temperature that is facilitated by electric current passage through a corresponding resistive heating element contained within the MNSDED or by Joule heating of the environment (e.g. interstitial fluid, plasma, etc.) immediately surrounding the barrier. In such embodiments, thermo-responsive materials will ideally be stable under physiologic temperatures (about 37° C.), and will have a melting transition temperature that is slightly higher that physiologic temperature (e.g. a transition temperature of 40° C. for poly(γ-2-(2-(2-methoxyethoxy)-ethoxy)ethoxy-ε-caprolactone)-b-poly(γ-octyloxy-ε-caprolactone, or glass transition temperature of 45° C. for poly(lactic-co-glycolic-acid) ("PLGA")). In other embodiments, the barrier may be composed of the polymer polypyrrole, which may be removed through electrochemical redox and electrical current. In other embodiments, the barrier may be composed of a phospholipid or PEG, which is porated upon simulation through an electric current or electric potential that is facilitated by the MNSDED IC. In yet other embodiments, the barrier may be composed of a polymer or other chemical or biological entity that is stable at physiologic pH (7.4), but whose stability is reduced at acidic pH, enabling membrane breakdown when the MNSDED is exposed to acidic pH, (e.g. if the MNSDED is intended to enter into an acidic compartment post administration, for example, a lysosomal compartment, tumor interstitium, or gastric mucosa). In these embodiments, the barrier material will ideally be stable at physiologic pH (7.4) and will disassemble at marginally lower (or higher) pH, (e.g. PEG-poly(beta-amino-ester) is stable at pH 7.4 but disassembles at pH 6.4-6.8).

The MNSDED reservoir may be constructed through lithographic and etching methods and techniques known to those skilled in the art of microelectronic manufacturing. Specifically, prior to functionalization of the EEBIPs with the aforementioned functional handles and EEBLs, the final layer of the MNSDED may be modified with trenches, holes, or any void of any shape as enabled through pre-designed lithographic patterning and post-lithographic etching. In some embodiments, the final layer of the MNSDED may be composed of interlayer dielectric material (that is not EEBIP associated) that is of any dielectric material (e.g. an oxide, usually an oxide of silicon or non-conductive oxide of another material). This oxide may be etched with a corresponding etching technique that has high selectivity for this dielectric material as is well-known to those skilled in the art of microelectronics manufacturing. Ideally, this etch will be facilitated by lithographic printing that protects the EEBIP from the etching process, and which enables geometries and dimensions that maximizes the surface area etched and depth of etch. In some embodiments, the MSNDED surface will be designed such that the reservoirs may be of sufficient size to encapsulate large chemicals or biomolecules (e.g. CAS9 and large sequences of genetic material such as DNA to deliver to and incorporate within an DAC genome), that may be, for example, no less than about 20 nm in major axis diameter for an ellipsoid-like entrance to a reservoir and no less than about 40 nm in depth. Once the reservoir has been etched, biocompatible lithographic functionalization (as described herein) of the EEBIPs may be executed, followed by the etching liftoff process (as described herein). In some embodiments, prior to addition of the linker that utilizes conjugate chemistry between the linker and the functional handles associated with the EEBIP, the reservoir may be filled with a therapeutic or imaging agent by immersing the MNSDED devices in solution with the therapeutic or imaging agent at a predetermined concentration (e.g. a concentration that is near the therapeutic or imaging agent solubility limit) that also contains the material from which the membrane will be composed at a concentration that enables the self-assembled formation of a membrane (at appropriate concentration, pH and temperature) across the external opening of the reservoir. Once the MNSDED has had sufficient time to encapsulate the therapeutic or imaging agent in the reservoir, the MNSDED may be separated from the solution (that contains therapeutic or imaging agent and membrane material) through serial centrifugation and removal of supernatant, or through another filtration method as would be known to those skilled in the art of nanoparticle synthesis. The MNSDED may then proceed with further conjugation chemistry that couples any linkers and EEBITAs as described further herein.

Following delivery of a MNSDED with filled reservoir to a subject, the EEBITA may facilitate the MNSDED association with a DAC. In some embodiments, the EEBITAs may be designed to target DAC receptors such that following binding of the MNSDED to the DAC, the MNSDED may be internalized by the DAC through an endocytotic or phagocytic process. The membrane of the loading compartment of the internalized MNSDED may be destabilized through the aforementioned methods in the phagocytic or endosomal/lysosomal environment (e.g. through pH catalyzed dissolution) and secrete the loaded agent, thereby delivering the agent to the target DAC. Alternatively, upon EEBITA binding of a specific pattern of DAC receptors, the MNSDED deciding subsystem may provide a corresponding output that activates the effecting subsystem, and upon power source initiation, the membrane of the loading compartment may be removed through the aforementioned methods, and the loaded agent may be secreted locally to the DAC near the DAC surface. In variants of this embodiment, upon activation of the effecting subsystem, in concert with the dissolution of the compartment membrane, the nanoneedles may have a voltage applied such that there is transient poration of the DAC BLM, where the released therapeutic or imaging agent may diffuse through the pores in the BLM.

In some embodiments the described methods may be carried out to deliver a chemotherapeutic agent, which may be used to treat a cancer. For example, in some embodiments, the described system, apparatus and method may be carried out to deliver a chemotherapeutic agent, for example, irinotecan or 5-fluorouracil (5-FU), which may be used to treat a cancer such as gastric adenocarcinoma. Other agents for use in treating cancers may also be delivered to cancer cells via the described system, apparatus, and methods. In other embodiments, a radioactive treatment may be delivered specifically to tumor cells through this method. In some embodiments the described methods may be carried out to deliver an antibiotic agent, which may be used to treat an infectious disease. In some embodiments the described methods may be carried out to deliver an immunosuppressant agent, which may be used to treat an autoimmune disease. Imaging agents that might not readily access the DACs on their own may also be delivered using the described methods. For example, in some embodiments the described methods may be used to deliver a MNSDED carrying the imaging agent $^{64}$Cu to DAC tissues of a subject to allow for imaging, namely through Positron Emission Tomography ("PET"). Further, the described methods may be used to deliver a combination of one or more therapeutic agents, imaging agents, or both therapeutic agents and imaging agents to pathogenic entities (including DACs and viruses) of a subject.

MNSDED Power Supply and Signaling Subsystem

The MNSDED may include a power supply and may contain a signaling subsystem, which are comprised of at least the following components and materials: (1) radiofrequency energy harvesting circuitry; (2) power regulation and distribution circuitry; and (3) signaling circuitry (depending on the use case).

Figure 19:
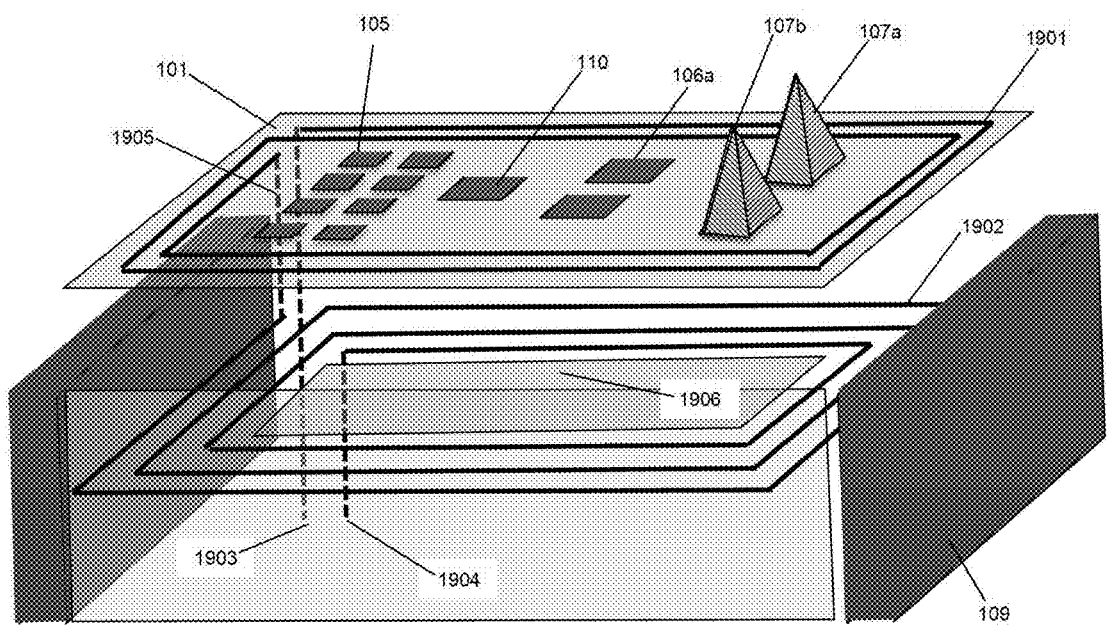
FIG. 19 illustrates an exploded view embodiment of a multilayer coil Radiofrequency Energy Harvesting Circuit ("RFEHC") embedded in the MNSDED.

Radiofrequency Energy Harvesting Circuitry ("RFEHC"):

MNSDED sensing, deciding and effecting subsystems will require supply voltages appropriate for the CMOS technology employed in their construction. These voltages may be supplied by harvesting radiofrequency ("RF") energy received through antenna(s), which will then be rectified and multiplied to a sufficient voltage to enable stable analog and logic circuit biasing and operation. The RF Energy Harvesting Circuit ("RFEHC") may include an inductor or one or more antenna(s), matching/tuning circuitry, rectifying and voltage multiplying circuitry and voltage regulating circuitry. An example of an approximate schematic and layout of such is illustrated in FIGS. 19 through 21.

Depending on the RF frequency or frequencies employed by the RFEHC, antenna structures may include a simple planar or multi-layer planar spiral loop(s) with multiple turns, or more complex dipole or other structures. The antenna efficiency (radiation resistance and internal loss) may be characterized by number of turns, geometry, and layout, as well as geometrically constrained antenna impedance.

Depending on antenna impedance ($Z_{ant}$), the RF voltage from the antenna may be passed through an impedance transforming network to ensure optimal recovery of the RF energy from the antenna into the rectifying/multiplying circuitry. Depending on the impedance requirements of the subsequent rectifying/multiplying circuitry, an impedance transform to a larger apparent real Z may be required (see FIG. 22).

Rectifying and voltage multiplying circuits are well known in the field of RF energy harvesting. A simple example is the lowpass T network, as would be known in those skilled in the art, which will boost the impedance of the planar spiral from a few mOhm to larger values.

A simple 8-stage rectifying and multiplying (voltage multiplier) circuit is illustrated in FIG. 21. The DC voltage needed will depend on the desired CMOS operating characteristics, process technology and total circuit power requirements, e.g., a MNSDED that is not required to transmit energy can make do with a smaller power budget. The number of multiplier stages may be determined by the available ambient HF incident power, the CMOS transistor and capacitor characteristics and connection parasitics.

Power Regulation and Distribution Circuitry:

The rectified output of the RFEHC may be fed "as is" (without conditioning) to the logic and communication circuitry of the MNSDED, as described herein, or it may be further conditioned using active or passive components, such as additional filtering capacitors, diodes and/or series pass regulator circuitry. Given the small circuit load of the MNSDED at a no more than 7 nm semiconductor node, additional regulation will likely be unnecessary, but could easily be implemented using either passive components, e.g. filtering capacitors or by active (e.g. mirror circuits, series pass regulation) by those familiar with conventional CMOS power deliver systems.

MNSDED Signaling from External Circuits:

In addition to supplying power to the MNSDEDs induced through an external RF power source, the RFEHC inductor may be used to receive information from an external signaling source such as a RF transmitter.

Antenna Structures and Matching Circuits:

MNSDEDs may also employ the RFEHC antenna or separate antenna structures to receive RF signals from external circuits. Receiving circuitry may include antenna structures, matching circuitry and receiver circuitry. For high frequency ("HF") frequencies (30 MHz and below) the small dimensions of the MNSDED and its immersion in a weakly conducting medium (e.g. blood, lymph or extracellular or intracellular fluid or cytosol) precludes more elaborate antenna structures other than simple loops because the MNSDED is much smaller than most radiofrequency wavelengths of interest. For THz to near infra-red ("NIR") frequencies there is the possibility of fabricating more complex antennas including but not limited to microstrip patch antennas, microbowties or similar structures. Both simple loops and more complex structures may be impedance transformed using standard T, Pi or other multi-element matching structures.

Signaling Circuitry:

MNSDEDs may also employ the same antenna, a portion of the RFEHC antenna or separate antenna structures to convey signals to external circuits. External signaling circuitry may include antenna structures, matching circuitry as for the receiver, and indeed may employ the same antenna structure(s) with the incorporation of diplexer/receiver protection circuitry. MNSDEDs may communicate to each other or an external transceiver using far field or near field (e.g. inductive coupling) methods. The transmitter circuitry required may be qualitatively similar for both methods. Signals encoded by phase/frequency modulation (e.g. quadrature phase shift keying ("QPSK")) techniques or simple pulse code modulation ("PCM") may be demodulated from a carrier frequency using standard FM or AM techniques. More sophisticated channel-sharing is also possible using code division multiple access ('CDMA") techniques, with a concomitant increase in receiver complexity and therefore direct current ("DC") power requirements. These techniques are well established in wireless communications and are familiar to those skilled in the field of radiofrequency communication.

Through the signaling circuitry, communication may occur between individual MNSDEDs as well from MNSDEDs to external circuits. External devices may be able to compile information from MNSDEDs and perform computation utilizing this information to generate clinically relevant insights or to guide a therapeutic action, either by a physician, or by real-time feedback to the MNSDED through the signaling circuitry. In certain applications, MNSDEDs may be designed to be sub-specialized, for instance, some MNSDEDs may only electroablate DACs and other MNSDEDs may electroporate and release a therapeutic locally at the DAC and yet another MNSDED may release an imaging agent when a DAC is bound and yet another MNSDED may call to other attract other MNSDEDs or act as a signal relay path from one MNSDED from an external or internal node. Each of these subspecialized MNSDEDs may, through signaling circuitry, communicate with each other, or with the external circuitry as described herein.

MNSDED Fabrication, Testing, Activation and Etch Lift-Off

The methods disclosed herein also outline key steps in the MNSDED fabrication and testing process. Summarized here are the methods including: the etch "lift-off" technique that involves etching the polysilicon layer underlying the MNSDED on the wafer in a bio-compatible manner and releasing the MNSDED from the wafer into solution; electrical testing ("e-testing") the MNSDEDs on the wafer with a voltage that is sufficient to disable all MNSDEDs with dysfunctional logic circuits, and leaving intact all MNSDEDs that are properly functioning; functionalizing each EEBIP with a unique EEBITA through bio-compatible lithographic techniques that allow for EEBIP-specific functional handles and EEBIP-specific EEBILs, specifically by employing EEBITAs and linkers that are undisturbed by a bio-compatible lithographic process (e.g. pH appropriate and chemically benign triple layers, resists, topcoats, developers, and other solvents, as well as appropriate materials to maintain biologically relevant temperatures during the Spin-Expose- Develop ("SED") process). Fabrication methods will also include selective polymer attachment (through methods including directed self-assembly).

Lithographic Techniques for Bio-Compatible Lithography in Creating the EEBI:

The methods provided herein include biocompatible lithographic techniques. One such technique is the utilization of ssDNA that is attached to the EEBIPs, which may then bind to a complementary ssDNA sequence that itself is bound to a targeting ligand. For example, a thiol-R-thiol bifunctional linker may be added to the wafer surface in aqueous solution to functionalize the surface of the metal EEBIPs with thiol groups. Once the EEBIPs have been functionalized with a thiol functional handle, select EEBIPs may be covalently linked to select DNA sequences, which may be accomplished through conjugation of ssDNA to the EEBIP-associated thiol group through a complementary functional handle to thiol that itself is covalently coupled to ssDNA (e.g. ssDNA-maleimide).

To accomplish this EEBIP-ssDNA sequence specificity, a predesigned group of EEBIPs may be left exposed during lithographic patterning through mask-based patterning, while covering with triple layer (described herein) all other EEBIPs that are to remain unreacted with the specific ssDNA sequence. This lithographic patterning may employ a triple layer (biological protection layer (e.g. SU-8, PEG, etc.), anti-reflective coating ("ARC"), and a photoresist ("PR") layer (e.g. ideally but not limited to known biocompatible resists such as SU-8) that may contain a top coat (e.g. if an immersion photolithography process is indicated)), materials that are well known to those skilled in the art of photolithography, and the lithographic patterning may be accomplished through a standard spin-expose-develop ("SED") process that is itself well known to those skilled in the art of photolithography.

Subsequently exposed EEBIPs may be treated with a ssDNA oligomer (cDNA as described herein) that contains a maleimide group at one end, which will react with the thiol functional handle that was previously coupled to the EEBIP surface, to create a thioester linkage between the EEBIP and the ssDNA oligomer. Once the ssDNA oligomer is datively and covalently linked to the EEBIP, the triple layers may be removed through conventional processing (including but not limited to processes that utilize biocompatible solvents that do not damage ssDNA, or other known solvents, for example, N-methyl-2-pyrrolidone (NMP), followed by solvent removal by heating to 80 C). The biocompatible protectant layer deposition, ARC deposition, PR deposition, SED, ssDNA conjugation, and PR/ARC removal process may be reproduced as many times as desired in order to add ssDNA oligomers of different, and possibly unique, sequences to strategically and photolithographically exposed EEBIPs. Once all the ssDNA oligomers have been added to the appropriate EEBIPs, the MNSDED may be liberated from the wafer surface through an etch-based lift-off process, utilizing a method of that will be described herein.

Some embodiments may require ssDNA as an EEBIL, as ssDNA is thermally stable at SED-relevant temperatures of up to, but not exceeding, about 90° C. for SED-relevant short time scales of minutes (evidenced by routine PCR protocols that take ssDNA to temperatures of 90° C. for periods of minutes), and ssDNA is acid stable relative to pH and time exposure conditions experienced during the SED process. The bioprotective layer that may surround ssDNA and that is added prior to ARC and SED will ideally maintain a pH neutral environment, and in addition to a standard bioprotective material (e.g. PEG), it may contain materials that act as proton sponges (e.g. including but not limited to amine containing polymers such as poly-L-lysine, poly(beta-amino esters), poly-(gamma-benzyl-L-glutamate), or polyhistidine).

Post etch "lift-off", the resulting colloidal suspension of MNSDEDs may be reacted with EEBITAs and reference ligands that themselves have been bio-conjugated to complementary sequences of DNA (as described previously herein) though bifunctional linkers. For example, in one embodiment, IgGs with reduced thiol groups may serve as EEBITAs and reference ligands and may react with DNA-maleimide to form a thioester linkage between the Fc portion of the antibodies and the cDNA fragments. Pre-prepared EEBITA-cDNAs and reference-ligand-cDNAs may be stirred in solution with the MNSDEDs. The subsequent coupling of the reference ligands and EEBITAs to their intended EEBIPs on the MNSDED will occur through complementary ssDNA (cDNA) sequences, where annealing of the complementary sequences of ssDNA can be thermally controlled so that the annealing takes place at no less than 5° C. below the melting temperature ($T_m$) of the complementary strands of ssDNA. For example, in some embodiments, the cDNA sequences may be designed so that the $T_m$ is 55° C., and the reaction mixture may be incubated between about 50° and about 55° C., where 50° C. is no more that 5° C. below the $T_m$, with the additional constraint that the temperature of the reaction does not exceed the temperature at which the ligands (EEBITAs and reference ligands) begins to degrade or denature (e.g. antibodies may begin to denature at about 55° C.). This EEBITA-MNSDED coupling reaction may be conducted in an aqueous environment, with a gently buffered solution (e.g. <50 mM sodium phosphate, pH 7.4). Once all complementary EEBITA and reference-ligand-associated ssDNA has been annealed with the EEBIP-associated ssDNA, the remaining surface of metal may be back-filled (e.g. with a methoxyl-(n-alkyl)-thiol monolayer) that will further protect the EEBIP from non-specific binding of environmental components (e.g. plasma proteins, interstitial proteins, etc.). Through this process, "EEBIP X" will associate with "ssDNA sequence X", which will anneal with "complementary ssDNA associated with sequence X", which is bound to "EEBITA X", where "X" refers to an intended association with a specific "receptor" on "DAC X", such that binding to "receptor X" will cause "EEBIP X" to have its associated latch triggered, which is associated with a logical output of the IC to respond appropriately to the binding of receptor X.

Additionally, in other embodiments, a pre-selected group of EEBIPs may be left exposed during lithographic processing through mask-based patterning as previously described. The exposed EEBIPs may be functionalized with a chemical functional handle (e.g. thiol) as previously described, and an EEBIL (ideally a conductive polymer as previously described) will be coupled to the functional handle (e.g. through a malemide-linker bioconjugate reaction), where the EEBIL itself is bifunctional with a separate and unique functional handle on its opposing end (e.g. an NHS-ester, a primary amine, or other chemically reactive moiety). This separate functional handle (e.g. an NHS-ester) will be unique to a complementary reactive group that is placed on the EEBITA (e.g. a primary amine on the EEBITA that can couple with the NHS-ester on the EEBIL). In a similar fashion to the complementary ssDNA strategy, the biocompatible protectant layer deposition, ARC deposition, PR deposition, SED, and PR/ARC removal process may be reproduced as many times as desired in order to add unique functional handles to select photolithographically exposed EEBIPs. Each unique functional handle may then be coupled to its corresponding EEBITA through its complementary reactive group as described herein. The combination of functional handles and their complementary reactive groups are described herein.

Each MNSDED may be fabricated on a silicon wafer (for example, a 300 mm wafer), in large quantities per wafer (for example, a hundred million or more MNSDEDs may be fabricated on a 300 mm wafer). In order to ensure that all MNSDEDs which are lifted off are either fully functional or disabled, the following electrical testing ("e-testing") and enabling/disabling circuitry and methods may be employed. In the case this e-testing is employed, these MNSDEDs will be non-functional until the devices have been tested and validated as functional. On the wafer, multiple MNSDEDs may be placed in a constellation around a signal sort test chip. This test chip may be probed with a standard sort probe card. The probe card may provide power to the test chip, which may then perform a preprogramed set of tests on each MNSDED (e.g. only fire for a combined EEBIP pattern of 011101) and may report back the success or failure of each MNSDED attached to it. The test chip may input test signals into test communication circuitry (described below) within the MNSDEDs, and if the MNSDED logic circuit passes the test pattern suites, then the test chip may fire that MNSDED's internal fuse, enabling the energy harvesting circuit of that MNSDED. In this embodiment, the MNSDED will be non-functional unless the internal fuse has been disabled.

This testing may assist with identifying a faulty MNSDED. For example, some of the EEBIPs may be designed to recognize tissues for which the MNSDED is not intended to impact. The testing may ensure that only those patterns associated with target tissues, and not off-target tissues, will activate and trigger the MNSDED logic circuit. For example, HER2/Neu positive gastric adenocarcinomas cannot be treated with both trastuzumab and anthroquinones simultaneously due to cardiotoxicity, as there is HER2 present on cardiomyocytes. A MNSDED strategy will allow for treatment of HER2 positive gastric adenocarcinoma, when the MNSDED is programed to be inactive when recognizing cadiomyocyte specific antigens. During the MNSDED testing and activating process, those MNSDEDs that have faulty circuitry associated with recognizing cardiomyocyte-associated antigens will fail the test and therefore the internal fuse will not be disabled, and the MNSDED will be non-functional or non-operable for its intended purpose. This will increase the safety profile of the MNSDED by enabling MNSDEDs that do not have off-target (i.e., unintended) effects.

The MNSDED wafer-level testing circuitry within each MNSDED may be attached to a test chip through metal line connections (providing at least for power, ground, transmit, receive, and fuse functions). The transmit and receive may be at least a two-wire communication bus to each chip, much like a serial bus. Each MNSDED may have an RFEHC as a portion of the power supply. The RFEHC may feed the power regulation circuit, which may then provide DC power to the remainder of the MNSDED. Each MNSDED may be fabricated with a fuse-able link between the output of the power regulation circuit and ground, effectively shorting the power supply to the chip, until the fuse is blown at test. This may help prevent creating a chip with faulty logic.

An MNSDED wafer may be fabricated as an array of test interface chips ("TICs)", which has multiple MNSDEDs placed in a second array around the TICs. There may be thousands of these TICs per wafer. Each TIC may have about hundreds to thousands of MNSDEDs attached through the metal lines.

Each MNSDED may contain a logic circuit associated with the fuseable link. The TIC may send a set of patterns to the logic circuit. If the logic circuit sends the appropriate response back through the serial bus, the fuseable link will be blown, thus enabling the MNSDED power supply subsystem.

Once fabrication and testing of the device are complete, each individual device may be protected with the biocompatible-protective surface coating material (e.g. high molecular weight PEG coupled through a functional handle, Parylene coupled to the MNSDED surface through CVD, etc.), and the MNSDEDs may be released from the substrate through standard etch-out lift off techniques. One such exemplary technique includes the following steps: (1) a trench will be created around the device through an etch process during fabrication and prior to addition of EEBITAs to the EEBIP; (2) the protectant biocompatible materials are then applied to the surface of the wafer lithographically such that the material covers only the surface of the MNSDED; (3) the wafer surface is then subjected to an etchant material (e.g. tetramethylammonium hydroxide ("TMAH")), which then will have selectivity to the underlying substrate under the MNSDED, in such a way that the etchant will undercut and release each MNSDED while being non-reactive with the protective layer; (4) the released MNSDEDs are washed of etchant material through serial centrifugation, supernatant removal, and aqueous buffer addition steps; (5) the MNSDEDs are stored for further processing under inert conditions after freeze-drying.

Exemplary MNSDED Method of Use and Operation

Therapeutically-effective MNSDED quantities will be experimentally determined through preclinical and clinical trials, and these quantities may vary depending on the specific disease being targeted, the degree of disease progression, and other characteristics specific to the subject, where the subject may be any animal, including, but not limited to, a human, mouse, rat, hamster, guinea pig, rabbit, cat, dog, monkey, donkey, cow, horse, pig, bird, reptile, and the like. In some embodiments, subjects may be administered at least one of the described MNSDEDs in a daily dose where the dose range is in proportion to the weight or surface area of the subject. The dose administered to the subject may also be measured in terms of total amount of at least one of the described MNSDEDs administered per day. For example, in some embodiments, a subject may be administered a plurality of at least one type or class of the described MNSDEDs per dose per day, as may be required to achieve a therapeutically relevant dose (e.g. multiple dosing may be required to achieve a clinically relevant outcome such as multiple intrarectal dosing for the elimination of a specific disease-causing bacteria in the gut flora). In other embodiments, for example, a subject may be administered a dose at least once per year, as may be required to ensure that active and stable MNSDEDs are located in the intracorporeal space in order to detect the recurrence of cancerous cells and also to signal to an extracorporeal device that this cancer has been detected. In yet other embodiments, for example, the described methods may be carried out so the MNSDEDs described herein are administered to a subject weekly, bi-weekly, monthly, bi-monthly, semi-annually, or annually as needed per the clinical or preclinical development program. Treatment may be initiated with smaller dosages that are less than the optimum dose followed by an increase in dosage over the course of the treatment until the optimum effect under the medical circumstances is reached.

The methods provided herein may be carried out by administering to a subject the MNSDEDs while suspended in a pharmaceutically acceptable carrier. Such carrier compositions are useful, for example, for administration to patients to treat cancers, autoimmune disease, and infectious diseases. The carrier compositions may be formulated as any of various preparations that are known and suitable in the art. In some embodiments, the carrier compositions are aqueous formulations. Aqueous solutions may be prepared by admixing the MNSDEDs in water or suitable physiologic buffer, and optionally adding suitable colorants, preservatives, stabilizing and thickening agents and the like as desired. Aqueous suspensions may also be made by dispersing the MNSDEDs in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives, for example, suspending agents (e.g., sorbitol syrup, cellulose derivatives, or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The carrier compositions may be in powder or lyophilized form for constitution with a suitable vehicle, for example, sterile water, physiological buffer, saline solution, or alcohol, before use.

The carrier compositions may be formulated for injection into a subject. For injection, the carrier compositions described may be formulated in aqueous solutions, for example, water or alcohol, or in physiologically compatible buffers, for example, Hanks's solution, Ringer's solution, or physiological saline buffer. The solution may contain one or more formulary agents, for example, suspending, stabilizing or dispersing agents. Injection formulations may also be prepared as solid form preparations which are intended to be converted, shortly before use, to liquid form preparations suitable for injection, for example, by constitution with a suitable vehicle, for example, sterile water, saline solution, or alcohol, before use.

The carrier compositions may be formulated such that they are in a final oral solution, capsule, pill, sprinkle, syrup, or any other standard oral formulation known to those skilled in the art. Additionally, the carrier composition may be formulated for inhalation through nebulizers or sprays.

Method of Use Example:

The foregoing example of a specific embodiment is illustrative only and is not intended to be limiting in any way and is described here to demonstrate a method by which a MNSDED may be administered, and by which the MNSDED may operate when administered to a subject. This example will describe how a MNSDED may be employed to treat a subject who has been diagnosed with a well-defined solitary brain metastasis from a primary breast cancer ("BMBC").

Step 1:

One or more MNSDEDs may be designed and formulated such that it is in a sterile solution that recapitulates the cerebrospinal fluid, e.g. calcium chloride dihydrate (1.0 mg); magnesium chloride hexahydrate (0.8 mg); potassium chloride (1.1 mg); sodium chloride (44.0 mg); sodium phosphate, dibasic, heptahydrate (0.55 mg); sodium phosphate, monobasic, monohydrate (0.4 mg); and 5 mL Water for Injection. The pH of the solution may be between about 6.0 to about 7.0, for safe intracerebral or intraventricular administration. The MNSDED itself may be designed with EEBITAs that recognize receptors that are identified to be specific to the BMBC cells (e.g. estrogen receptor ("ER"), human epidermal growth factor receptor ("HER2"), and others), and the MNSDED may be designed so that it will electroablate any cells that it identifies (through a detected, predetermined EEBITA binding event) as having said specific BMBC cell surface receptors expressed on the surface of its membrane.

Step 2:

One or more MNSDEDs may be administered through direct, stereotactically enabled, injection into the intraventricular, intracerebral, or intratumoral space. This administration will require aseptic technique and should be administered by a physician knowledgeable in intracerebral or intraventricular administration techniques. The MNSDEDs may be administered directly into the cerebrospinal fluid, brain parenchyma, or within the tumor itself by single injection or infusion via a surgically implanted reservoir and catheter (intracerebro-ventricular device). The recommended dosage will be determined through one or more clinical safety, toxicity, and efficacy trials, that will themselves be directed by non-clinical good laboratory practice safety and toxicity studies. The MNSDEDs may be administered through infusion of the aforementioned intraventricular electrolytes with the MNSDEDs in combination with pre-treatment with any of antihistamines, antipyretics or corticosteroids. Each infusion will be formulated in a vial that is sufficient for one administered dose, and the complete infusion will be administered using an infusion set with a filter that is no less than 0.5 μm greater than the MNSDED characteristic size (e.g. a 2 μm filter may be required for a MNSDED that is 1.5 μm in size. Following complete infusion of the vial, intraventricular electrolytes may be used to flush the infusion line, port needle, and intraventricular access device in order to fully administer the dose.

Step 3 (Sensing):

In the case that one or more MNSDEDs is directly administered into the intratumoral space, the MNSDEDs will be allowed to travel through the intratumoral space (e.g. through diffusion), or its transport through the tumor may be assisted through additional infusion of intraventricular electrolytes (i.e. assisted convective transport). The MNSDEDs may be allowed to travel through the tumoral space for a minimum time span that is determined to be therapeutically effective, or longer, in order to enable the MNSDEDs sufficient time to interact with the tumor cells and associate with the target BMBC cell surface receptors. During this time, one or more EEBITAs on each MNSDED will attach to the associated BMBC cell surface receptors. For example, an EEBITA targeting ER will bind to BMBC cell surface ERs. In this case, EEBITA-ER association may facilitate HER2 binding to MNSDED associated HER2-EEBITA, through immobilization of the MNSDED on the BMBC surface followed by HER2 diffusion toward the associated EEBITA on the MNSDED through a fluid-mosaic diffusive process.

Step 4 (Powering):

Once the MNSDEDs have had sufficient time to associate with the BMBCs, the subject may be placed in an RF field (for example, an MRI machine, the MRI itself being an RF source), and under supervision of a physician knowledgeable in chemotherapeutic treatments, the subject may be exposed to electromagnetic ("EM") radiation in the radio-frequency range of the EM spectrum that is of sufficient strength to induce power in each MNSDED. The EM radiation is "harvested" or mediated through the aforementioned one or more RFEHCs within each MNSDED. The RF power and or frequency may be tuned or modulated in this case so that each MNSDED has sufficient power to electroablate the BMBC cells as will be described in the subsequent steps.

Step 5 (Deciding):

The MNSDED, in this embodiment, will be designed so that it will activate an electroablation mechanism if, and only if, the MNSDED EEBITAs associated with ER, HER2 and any other pre-defined BMBC-specific surface receptors are bound. On any one of these binding events, the reference-to-target EEBIP voltage difference will be amplified through a differential amplification circuit, that itself is powered through the aforementioned RF-induced power mechanism. If the sense amplifier detects a voltage difference that is above a predefined threshold, it will trigger an integral latch that will send an electronic signal to the MNSDED logic circuit that a DAC binding event has been achieved. This logic circuit will gate the powering of the effecting subsystem, which in this case will initiate an electroablative event to be described in subsequent steps. If this logic circuit has input from a predefined combination of latches that are associated with the identification of the binding of all required BMBC-specific receptors, then the logic circuit will trigger the effecting subsystem.

Step 6 (Effecting):

Once the effecting subsystem is activated, it will be powered through the aforementioned RF-induced power mechanism, that is assisted through a voltage amplifier and capacitor, that will release a conventional current through the MNSDED nano-needle cathode. This cathode will be designed so that it can deliver an electric current across the BMBC bilipid membrane, and the MNSDED circuitry and RF power will be designed such that the current is sufficient in both voltage and duration to irreversibly ablate the bilipid membrane. An MNSDED nano-needle anode will be situated on the MNSDED such that it is as distant on the MNSDED from the cathode needle as practicable, and such that it can complete the electronic circuit initiated by the cathode nano-needle and conducted through the BMBC bilipid membrane and cytosol.

Step 7 (Concluding Treatment):

Once sufficient RF power has been administered to the subject to ablate all BMBC cells that have been bound by the MNSDEDs, the patient may be removed from the MRI machine, and the intracerebro-ventricular device may be left in place for additional infusions of MNSDEDs, or the intracerebro-ventricular device may be removed if a physician knowledgeable in oncology determines that the device is no-longer indicated. Multiple doses of RF may be required within one session to optimally ablate all MNSDED bound BMBCs, and additionally, multiple infusions followed by multiple RF doses may be required to ablate the entire tumor and eliminate all associated BMBC cells.

Step 8 (Monitoring):

Once the course of MNSDED administration has been completed, the patient may be monitored for a predetermined set of time (likely months to a year) in order to determine if there is BMBC recurrence or any adverse reactions associated with the administration of the MNSDEDs in the CNS. MNSDEDs may remain in the space where the tumor had been ablated to serve as 'sentinels' that may detect the binding of other cancer cells, if they were to recur. In some designs, information regarding the 'bound' status of the MNSDEDs may be probed through RF signaling from the MNSDEDs, and an oncologist may monitor for any additional recurrence of BMBC cells, even prior to the formation of tumors that may be large enough to view through standard CT or MRI imaging. In the case additional BMBC cells are identified, an additional RF dose may be applied, repeating steps 4 through 8.

Referring now to the drawings, FIG. 1 illustrates exemplary geometry and surface features of a MNSDED. In this embodiment, the MNSDED has a spheroidal or cuboidal geometry associated with the etch-liftoff process, and MNSDED surface 101 associated with the wafer surface in which the MNSDED was fabricated. MNSDED surface 101 is substantially flat. In general, the MNSDED may be characterized by a MNSDED major axis length 103 and a MNSDED minor axis length 104 and has a MNSDED thickness 102 (z-height). MNSDED surface 101 contains a plurality of EEBI pads 105a-h, which are electrically conductive areas; a plurality of MNSDED communication bus pads 106a-b, which are electrically conductive areas that allow the MNSDED to communicate electrically to a test process; and a plurality of nanoneedle pairs 107a-b, comprised of nanoneedles 107a and 107b, which project up substantially from MNSDED surface 101. MNSDED bottom 108 of the MNSDED is comprised of a material which is not susceptible to the action of an etch liftoff chemistry, and MNSDED sides 109 may be made of a different material which is also resistant to the liftoff chemistry and provide a substantially hermetic seal for the sides of the device. The MNSDED top surface 101 also contains a solution-to-bulk silicon connection pad 110, which serves as a potential "ground" reference for electrical measurements with respect to cell surfaces or other surfaces or objects in the biological solution with the MNSDED. Solution-to-bulk silicon connection pad 110 may be coated with a conductive polymer or a polyelectrolyte layer to modify its electrical properties in solution. Solution-to-bulk silicon connection pad 110 may be electrically connected to the bulk silicon of the MNSDED.

Figure 2:
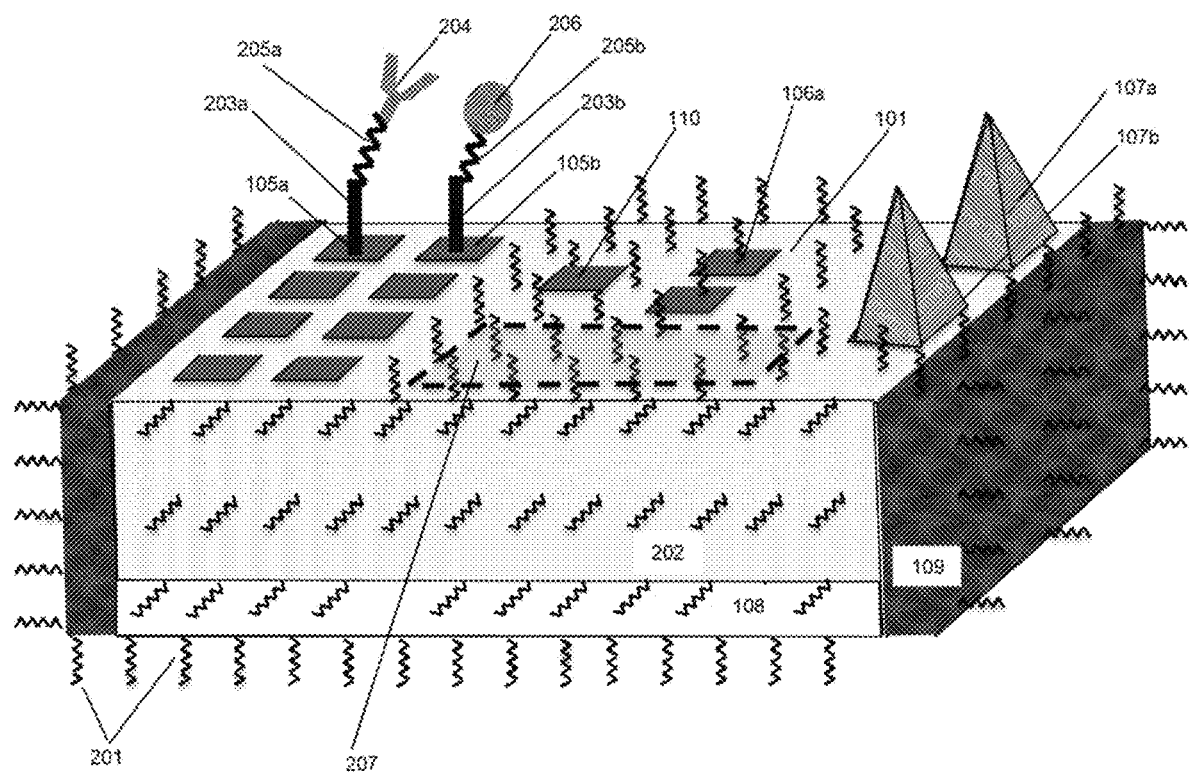
FIG. 2 illustrates an exemplary architecture and layout of a MNSDED.

FIG. 2 illustrates an exemplary architecture and layout of a MNSDED, including features and components associated with the MNSDED surface. FIG. 2 depicts the following design components: MNSDED bottom 108, comprised of a silicon-oxide or other insulating layer upon which the MNSDED is fabricated; a plurality of biocompatible protective molecules 201; and integrated circuitry layers 202 that are built on a Silicon-on-Insulator ("SOI") wafer through a microelectronic manufacturing processes. MNSDED surface 101, which is comprised largely of a non-conductive material such as silicon-oxide or any other dielectric, includes a plurality of EEBI pads 105a-h, each of which is coupled to the integrated circuitry, and a plurality of MNSDED communication bus pads 106a-b, each of which is coupled to the integrated circuitry. Functional handles 203a-b are bound to exemplary EEBI pads 105a-b respectively and serve to bind the electrically conductive linkers (EEBILs) 205a-b to the EEBI pads 105a-b. With respect to EEBI pad 105a, a target binding molecule (EEBITA) 204 is bound to EEBIL 205a. With respect to EEBI pad 105b, a reference molecule 206 is bound to EEBIL 205b. Electrically conductive nano-needle pair 107a-b is associated with an integrated circuit and is comprised of nanoneedle 107a, which is an anode, and nanoneedle 107b, which is a cathode. An optional loading compartment 207 may contain a therapeutic or imaging agent. MNSDED sides 109 are comprised of a material such as silicon nitride that provide a substantially hermetic seal for the device.

Figure 3:
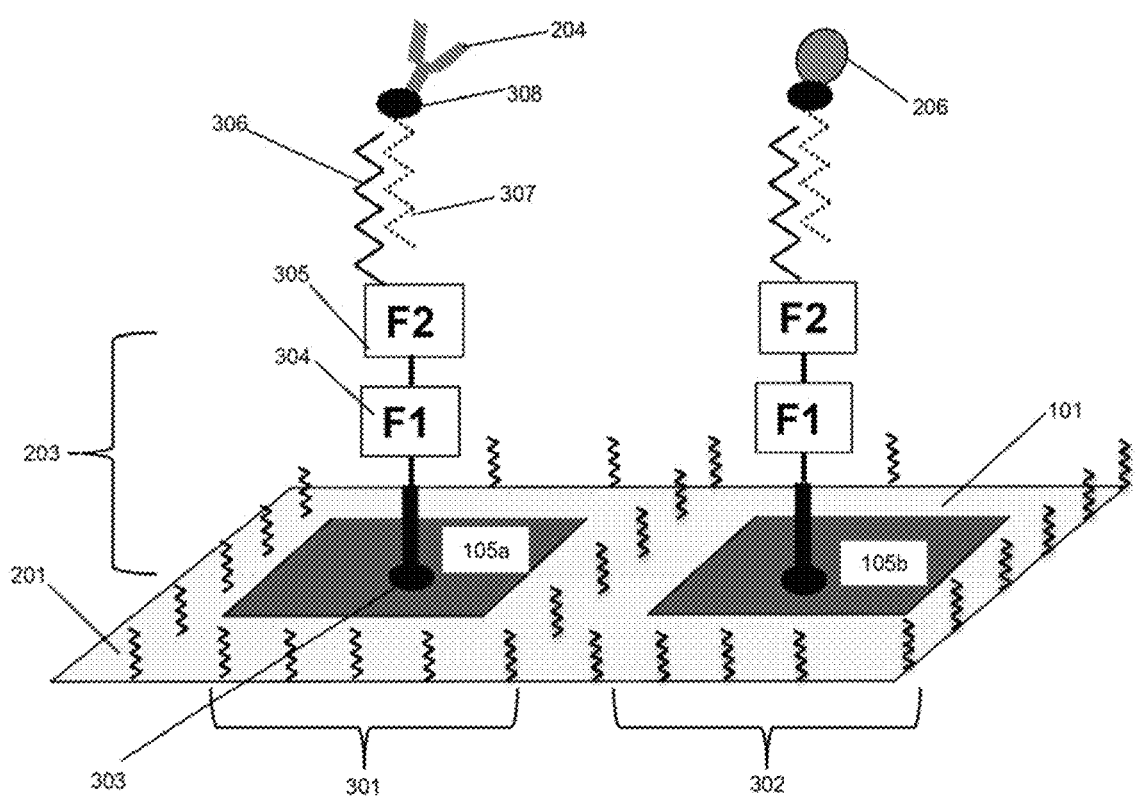
FIG. 3 illustrates an exemplary architecture and layout of a MNSDED sensing subsystem.

FIG. 3 illustrates an exemplary architecture and layout of a MNSDED sensing subsystem, and features and components thereof. Two environmental-electronic-binding-interfaces ("EEBIs") 301 and 302 are each comprised of an assembly of features and components of the MNSDED that are associating with, interacting with and sensing the surrounding environment. These assemblies transfer chemical or biochemical information from the environment to other components of the MNSDED by converting chemical or biochemical information into an electrical signal that the MNSDED logic circuitry can process. EEBI 301 is a targeting EEBI and has the following features and components: at least one electrically conductive EEBIP 105a; a plurality of biocompatible protective molecules 201 (only one of which is labeled for purposes of clarity) that surrounds the perimeter the EEBIP 105a to prevent biofouling or corrosion; a metal linking compound 303 that is homo- or hetero-functional in nature, and that is capable of datively binding to the gold or other metallic surface of the EEBIP 105a. Metal linking chemical moiety 303 serves to covalently or datively attach a second chemical moiety, 304, to the EEBIP 105a, (where 303 and 304 together are components of the homo- or hetero-functional handle 203). Chemical moiety 304 is itself a functional group that may be bound through conjugate chemistry to a complementarily reactive moiety 305, which itself is covalently attached to the EEBIL. This EEBIL may be of any electrically conductive polymer or material, and for clarity in this exemplary figure, it is a single-stranded DNA (ssDNA) 306. A second piece of ssDNA, 307, is rigorously complementary to ssDNA 306, and this ssDNA 307 is bound to ssDNA 306 in the finished device. At the distal end of ssDNA 307 is a chemical moiety 308, which facilitates chemically reactive chemistry or bioconjugate chemistry as would be known to those skilled in the art. Moiety 308 binds ssDNA 307 to targeting agent (EEBITA) 204. On any given EEBIP, such as 105a, there may be multiple instances of metal linking chemical moieties 303 bound to the gold or other metallic surface of the EEBIP, whereby each instance of metal linking chemical moiety 303 on the EEBIP serves to attach a chemical moiety 304 to the EEBIP. Each instance of chemical moiety 304 linked to the EEBIP enables attachment of an individual EEBIL (for example ssDNA 306 and a complementary ssDNA 307), and subsequently targeting agent binding moiety 308 bound to EEBITA 204. In that manner, multiple EEBITAs may be attached or linked to the same, single EEBIP. EEBI 302 is a reference EEBI and is nearly identical to targeting EEBI 301 except, in place of an EEBITA molecule 204, reference EEBI 302 includes a non-binding reference agent, 206, which has electrochemical properties similar to 204 as described herein.

Figure 4:
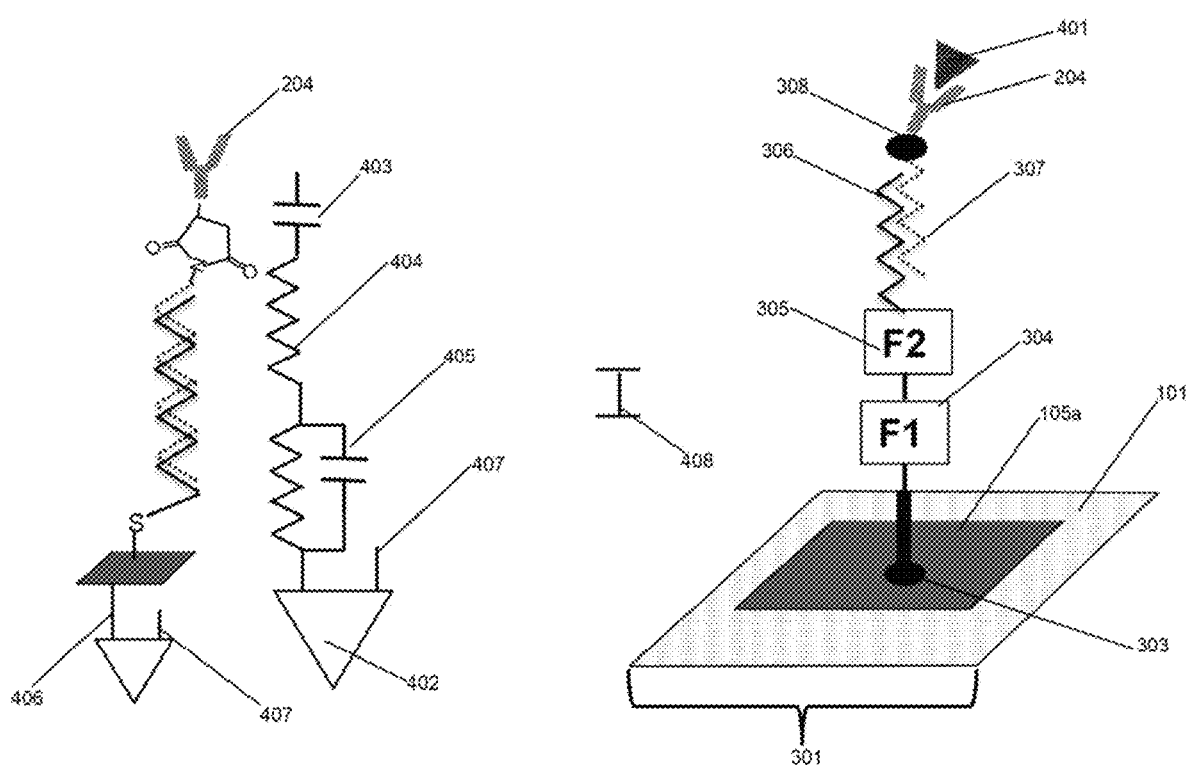
FIG. 4 illustrates an exemplary design and the resistor-capacitor ("RC") equivalent circuit of an EEBI that utilizes DNA as the charge-carrying polymer.

FIG. 4 illustrates the RC equivalent circuit of an exemplary EEBI design that utilizes DNA as the charge-carrying polymer. The components include: an EEBIP 105a which resides on the MNSDED surface 101 with a conductive area that is electrically connected to integrated circuitry below the surface; a metal linking chemical moiety 303; a chemical moiety 304 that has complementarily reactive moiety 305; an electrically conductive EEBIL that in this exemplary figure is comprised of a first ssDNA 306 and a second ssDNA 307, which comprise complementary sequences. The first ssDNA strand 306 is coupled to the linking moiety 305, and the second ssDNA strand 307 is coupled to a target binding molecule (EEBITA) 204 through a binding moiety 308. EEBITA 204 is able to specifically bind to a target antigen 401.

The double-stranded combination of ssDNA 306 and ssDNA 307 provides a path for charge flow arising from EEBITA 204 binding to target antigen 401. EEBIP 105a provides a connection to the integrated circuitry and associated sense amplifier circuitry 402, which is capable of detecting a change in capacitance or voltage upon binding of target antigen 401. An equivalent electrical circuit model of the arrangement of EEBI components (105a, 303, 304, 305, 306, 307, 308, 204) is given by the circuit comprised of capacitor 403 in series with resistor 404 and the parallel RC circuit 405. The combination of binding moiety 308 and EEBITA 204 is represented by capacitor 403. Resistor 404 accounts for the conductivity of the DNA formed by ssDNA 306 and ssDNA 307, or other electrically conductive polymer "wire". Parallel RC circuit 405 accounts for metal linking moiety 303, and chemical linking moiety 304 with its complementarily reactive chemical moiety 305. Conductive EEBIP 105a is connected to the sense amplifier circuitry 402 using standard integrated circuit technology. The other input to sense amplifier circuitry 402 is from conductive EEBI pad 105b, which is part of reference EEBI 302. A first voltage input to the sense amplifier circuitry 402 arising from EEBITA 204 binding to target antigen 401 (i.e., associated with targeting EEBI 301) is target voltage 406, and a second voltage input to the sense amplifier circuitry 402 arising from reference molecule 206 (i.e., associated with reference EEBI 302) is reference voltage 407.

Figure 5:
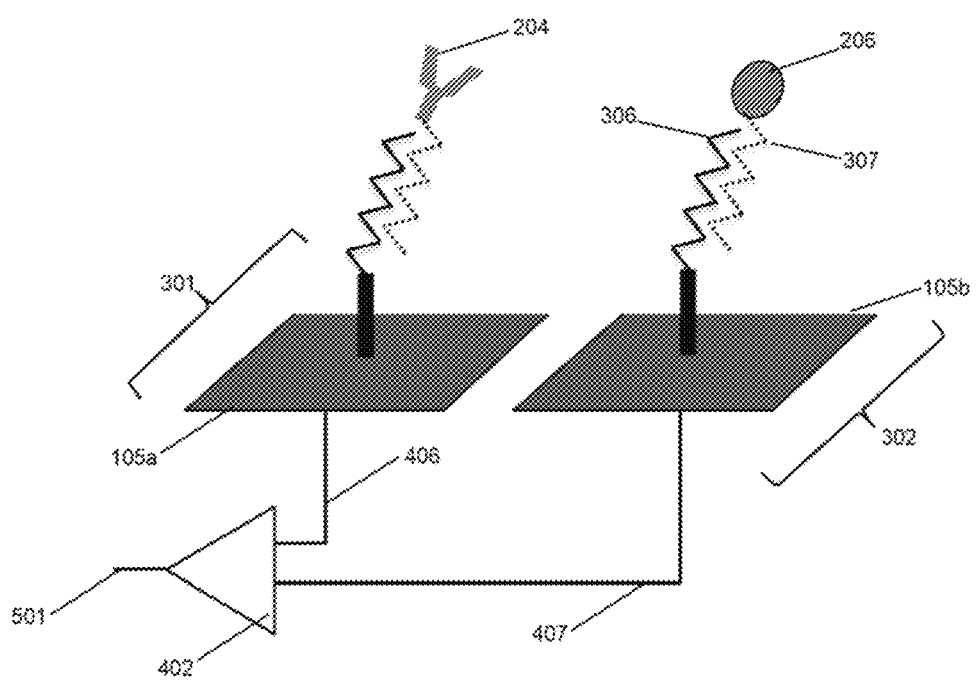
FIG. 5 illustrates a general exemplary architecture and layout of an EEBI molecular trim pair that includes one reference EEBIP.

FIG. 5 illustrates a general exemplary architecture and layout of an EEBI molecular trim pair ("EEBIMTP"). The components include: a targeting EEBI 301 that includes a target EEBIP 105a and an associated EEBITA 204; a reference EEBI 302 that includes a reference EEBIP 105b and a reference molecule 206; sense amplifier circuitry 402 that has a first input target voltage 406 from the target EEBIP 105a and a second input reference voltage 407 from the reference EEBIP 105b. The sense amplifier circuitry 402 has an output voltage 501.

Figure 6:
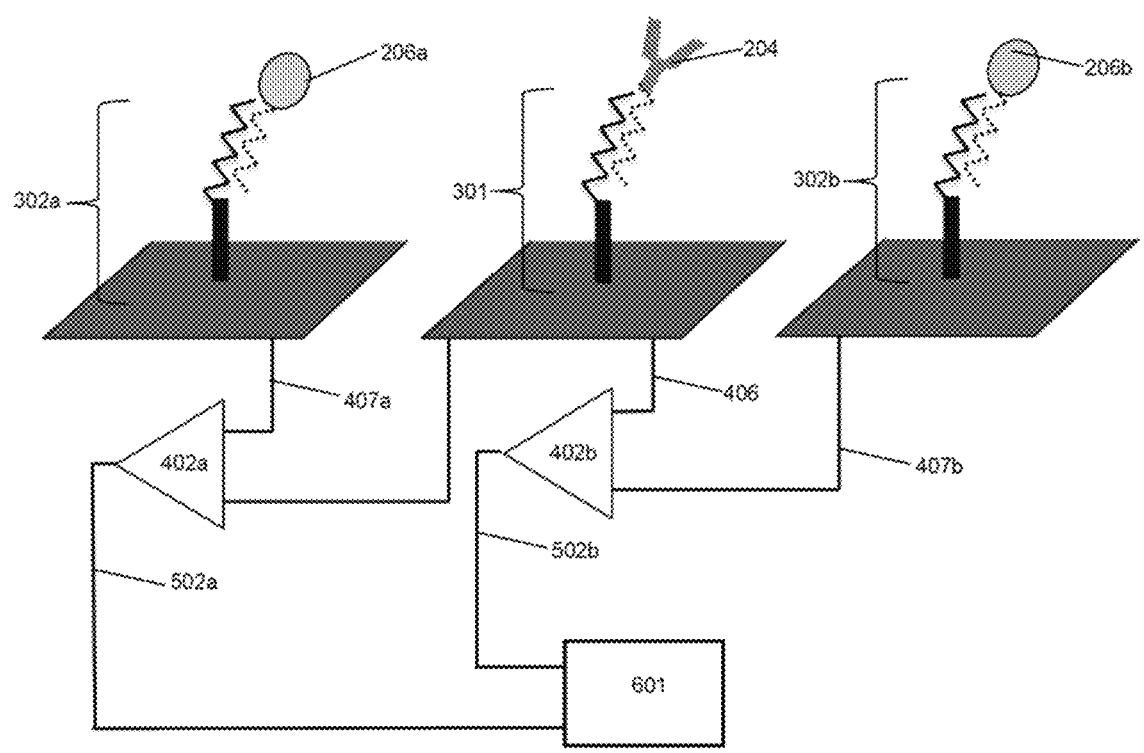
FIG. 6 illustrates a general exemplary architecture and layout of an EEBIMTP coupled to two reference EEBIs.

FIG. 6 illustrates a general exemplary architecture and layout of an alternative EEBIMTP, including features and components thereof, coupled to two reference EEBIs 302a and 302b. The features and components include: a first reference EEBI 302a that is associated with a first reference molecule 206a and reference voltage 407a; a second reference EEBI 302b that is associated with a second reference molecule 206b and reference voltage 407b; a targeting EEBI 301 that is associated with an EEBITA 204 and target voltage 406; a first sense amplifier circuitry 402a with voltage inputs 407a and 406 and a first sense amplifier circuitry output voltage 502a; a second sense amplifier circuitry 402b with voltage inputs 407b and 406 and a second sense amplifier circuitry output voltage 502b. The output voltages 502a and 502b representing binding events feed into a logic gate circuit 601, which can be any 2-input logic gate.

Figure 7:
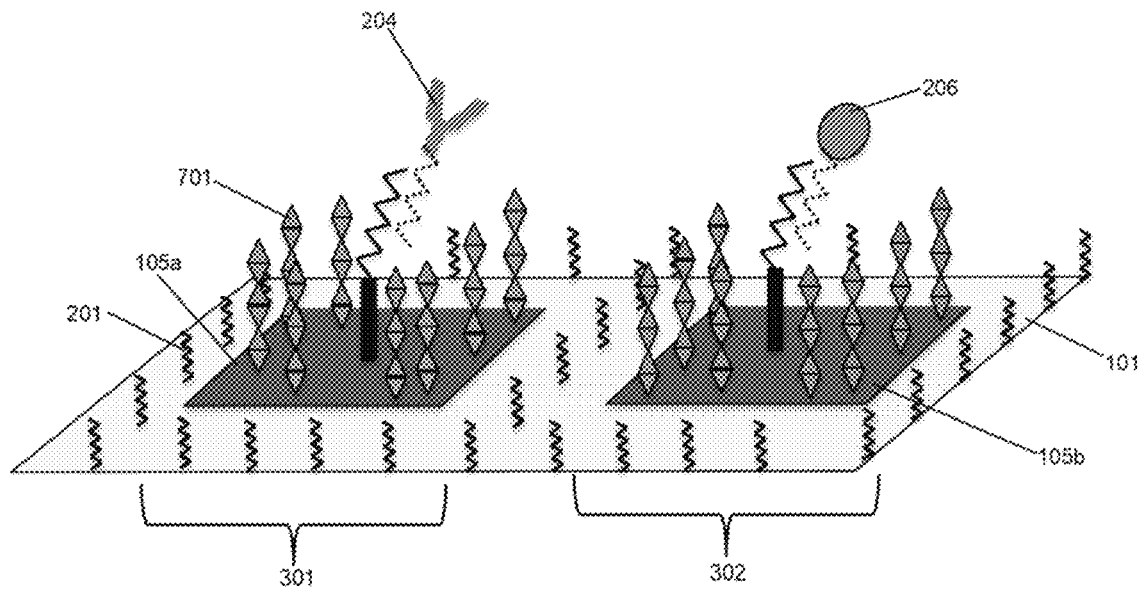
FIG. 7 illustrates an embodiment of EEBI gaskets associated with the MNSDED sensing subsystem.

FIG. 7 illustrates EEBI gaskets associated with the MNSDED sensing subsystem of certain embodiments. The components include: targeting EEBI 301 (including its respective EEBIP 105a coupled to EEBITA 204) and reference EEBI 302 (including its respective EEBIP 105b coupled to reference molecule 206); a plurality of biocompatible protective molecules 201 on the MNSDED surface 101 to prevent biofouling or corrosion; and a plurality of molecular gasket molecules 701 deposited on the periphery of the EEBIP 105a and 105b that create a privileged environment to modify and assist the EEBITA in binding and sensing.

Deciding Subsystem/Powers Supply/Signaling Subsystem

Figure 8A:
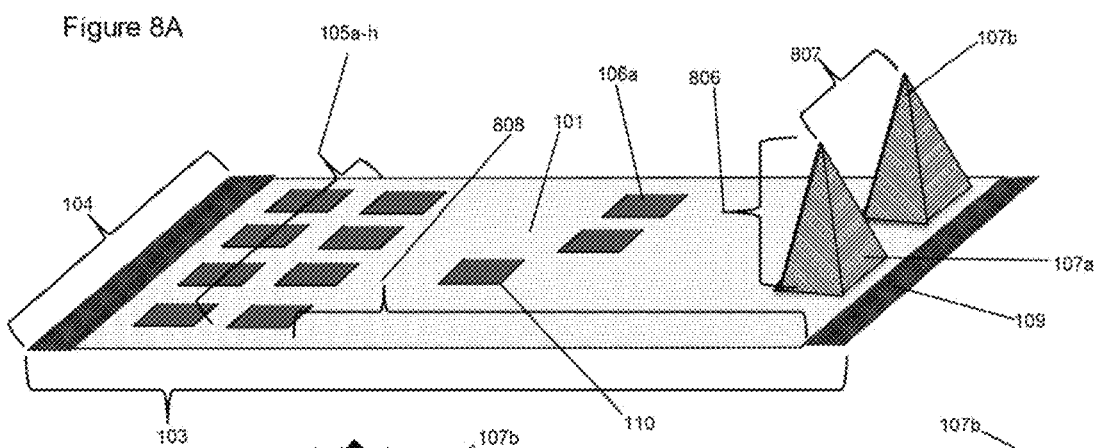
FIGS. 8A-8C illustrate a general exemplary architecture, layout, and equivalent circuit of one embodiment of the MNSDED effecting subsystem, including electroporation/electroablation nano-needles.
Figure 8B:
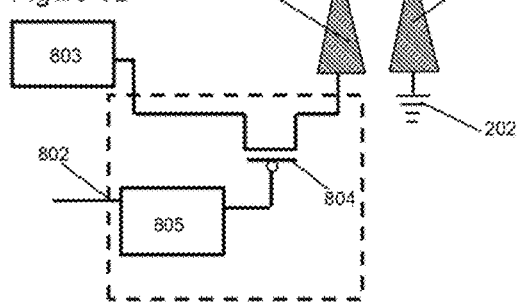
Figure 8C:
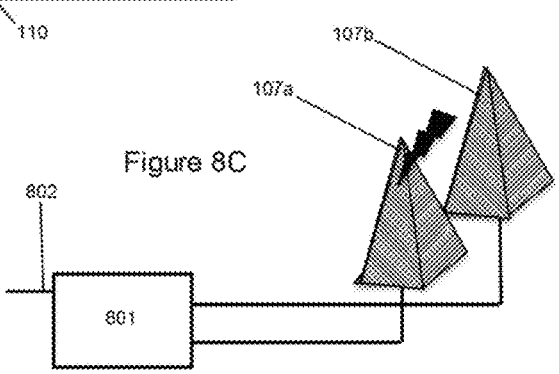

FIG. 8A illustrates a general exemplary architecture and layout of one embodiment of the MNSDED effecting subsystem, including electroporation/electroablation nanoneedles and other features and components of the effecting subsystem. As shown in FIG. 8A, nanoneedles 107a and 107b project from the MNSDED surface 101 with characteristic height 806. The nanoneedle bases are no more than characteristic spacing 807 apart, and each nanoneedle base is at least an offset distance 808 from the EEBIP array 105a-h. A simple implementation of a nanoneedle driving circuit is illustrated in FIG. 8C, with components and features that include: one or more nanoneedle pairs, each pair comprised of a nanoneedle anode 107a and a nanoneedle cathode 107b, with each nanoneedle pair 107a and 107b connected to a nanoneedle driving circuit 801 controlled by a logic input or inputs 802. In a simple example shown in FIG. 8B, the nanoneedle driving circuit 801 of FIG. 8C is represented by field effect transistor (FET) switch 804 and FET-activating circuit 805 (surrounded by the dashed box). One needle is connected to a nanoneedle driving circuit power supply 803 through FET switch 804, which is referenced to the substrate 202 and activated by FET-activating circuit 805, which is controlled by nanoneedle driving circuit logic input 802. The combination of FET switch 804 and FET-activating circuit 805 in FIG. 8B act to impose a voltage between nanoneedle 107a and nanoneedle 107b under control of the MNSDED logic (through logic input 802). Referring back to the implementation shown in FIG. 8C, the nanoneedle driving circuit 801 may alternatively incorporate a more complex gate-driver circuit that is capable of generating more complex waveforms.

Figure 9:
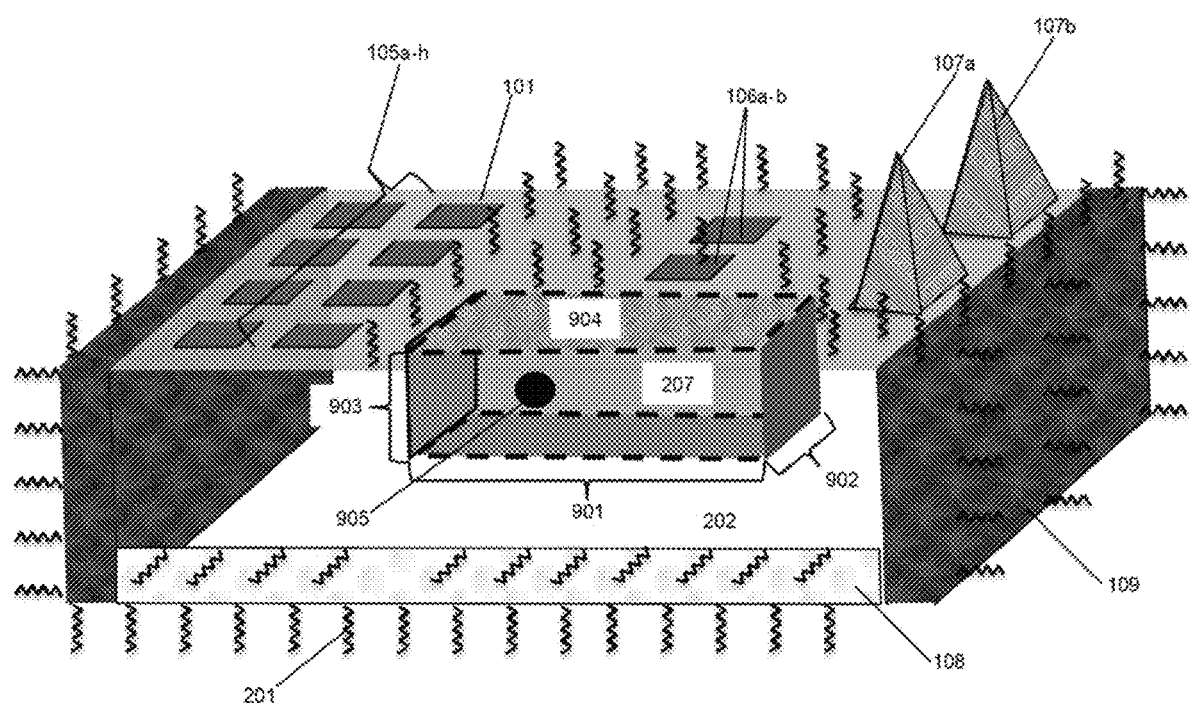
FIG. 9 illustrates a general exemplary architecture and layout of one embodiment of the MNSDED effecting subsystem, including drug/imaging agent delivery components.

FIG. 9 illustrates a general exemplary architecture and layout of one embodiment of the MNSDED effecting subsystem, including drug/imaging agent delivery components and other features and components of the effecting subsystem. The components and features include: one or more loading compartments or reservoirs 207, each said reservoir being a cavity having a characteristic dimension of reservoir length 901, reservoir width 902, and reservoir height 903, and each said loading compartment or reservoir 207 located in proximity to other MNSDED surface features including nano-needles 107a and 107b and EEBIP array 105a-h and MNSDED communication bus pads 106a and 106b. Each reservoir 207 includes a reservoir barrier 904 that is controllably removable through MNSDED logic circuitry (through dissolution or electrochemical transformation process), which seals or maintains a volume of drug or imaging agent 905 within the reservoir 207. The MNSDED surface is covered by a plurality of biocompatible protective molecules 201 and in this example has oxide MNSDED bottom 108 and nitride MNSDED sides 109.

Figure 10:
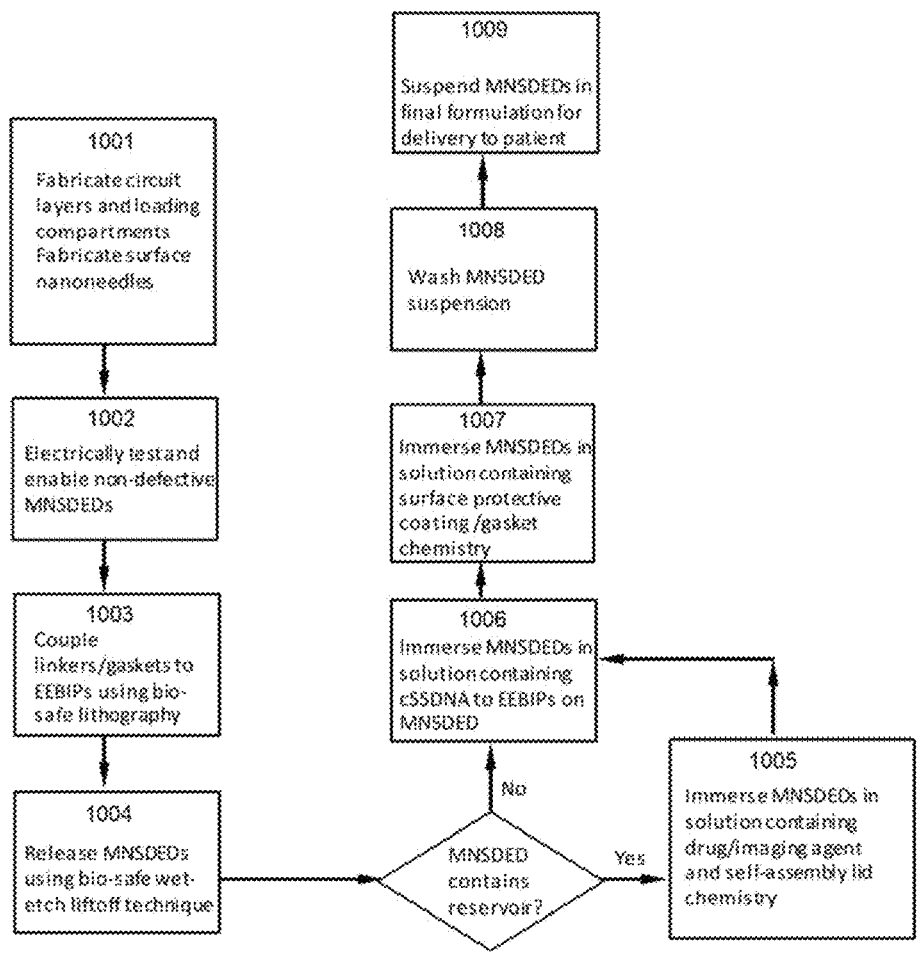
FIG. 10 is a flow diagram of an exemplary process for fabricating one or more MNSDEDs.

FIG. 10 is a flow diagram of an exemplary process for fabricating one or more MNSDEDs, and preparing those MNSDEDs that pass electrical testing for delivery to a patient. Variations to and deviations from this exemplary process for fabricating and preparing MNSDEDs, depending on specific MNSDED end-uses and applications, should be readily apparent to one of ordinary skill. In step 1001, the physical components and structures associated with a functional MNSDED design, including field effect transistors (FETs), contacts, metals, vias, capacitors, loading compartment(s), associated interlayer dielectric (ILD) layers, and nanoneedles are fabricated using a <10 nm technology node or process technology (as might be rated by the International Technology Roadmap for Semiconductors (ITRS)). In step 1002, after the nanoneedles are synthesized, each MNSDED undergoes electrical testing, as described in greater detail herein, to enable non-defective MNSDEDs for future administration and use. Conversely, defective MNSDEDs are not enabled. In step 1003, charge-carrying linkers (e.g. ssDNA) are coupled to EEBIPs utilizing bio-safe lithography techniques. In particular cases where the MNSDED uses a gasket, the associated gasket boundary region may be printed using bio-safe lithography with coupling of the gasket-associated functional handles at this time. In step 1004, the MNSDEDs are then released from the silicon wafer on which the MNSDEDs were fabricated using a bio-safe wet-etch liftoff technique that is described in greater detail herein. If the particular MNSDED design or use case requires delivery of a drug, imaging agent and/or other therapeutic, then in step 1005 the MNSDED loading compartment or reservoir is filled. In this step the MNSDEDs are immersed in a solution containing the drug, imaging agent and/or other therapeutic, and a "lid" (e.g., membrane) to contain the drug, imaging agent and/or other therapeutic within the loading compartment or reservoir is added through self-assembly. Regardless of whether the particular MNSDED design or use case requires delivery of a drug, imaging agent and/or other therapeutic, in step 1006 the MNSDEDs are immersed in solution containing complementary ssDNA that attach to the ssDNA bound to EEBIPs, previously added. In step 1007, the MNSDEDs are then immersed in solution containing surface bio-compatible protective agents, providing biocompatible protective molecules to the MNSDED surfaces. In the particular case that the MNSDED contains a gasket, the associated gasket molecules will be placed in solution at this time in step 1007 as well. In step 1008, the MNSDEDs are then washed or rinsed in a wash suspension. Finally in step 1009 the MNSDEDs are prepared for delivery to the patient by suspending the MNSDEDs in a final formulation medium, the composition of which may vary depending on the specific end use or application for these particular MNSDEDs.

Figure 11:
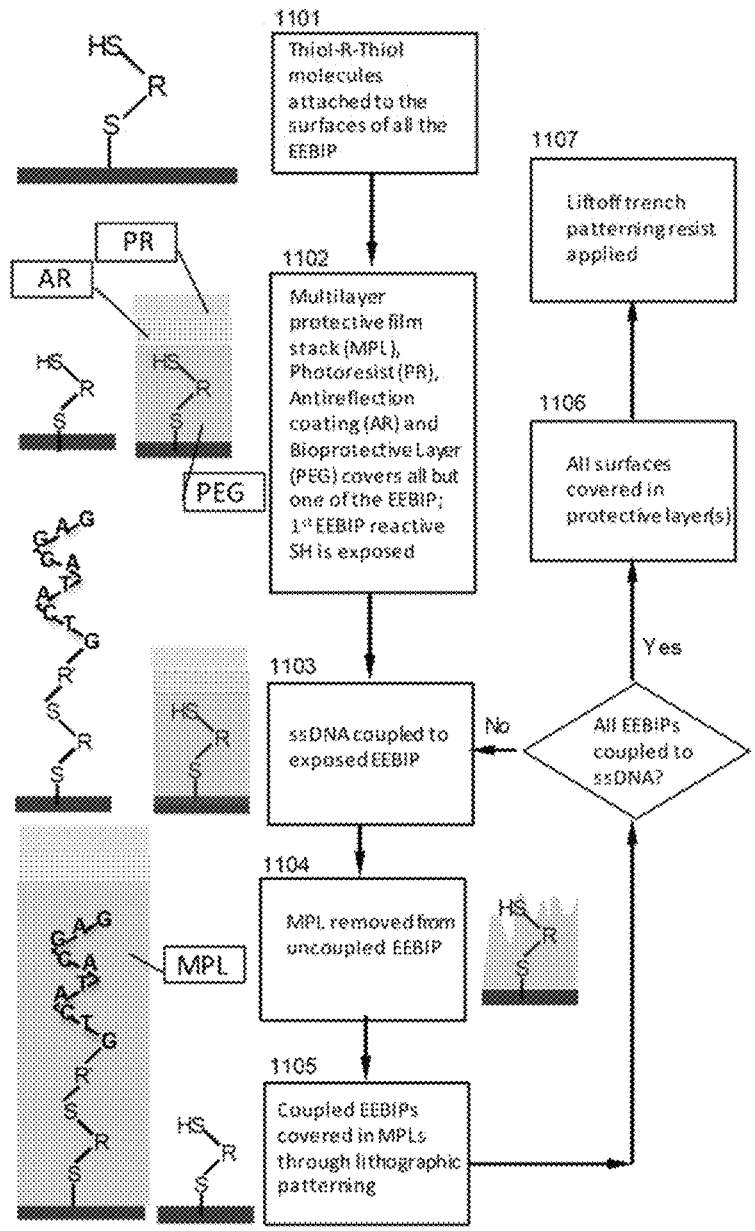
FIG. 11 is a flow diagram of an exemplary bio-compatible lithography process to fabricate an MNSDED.

FIG. 11 is a flow diagram of an exemplary bio-compatible lithography process to fabricate one or more MNSDEDs. Exemplary chemical structures and reactions, corresponding to the bio-compatible lithography process steps, are also depicted in FIG. 11. Variations to and deviations from this exemplary process for fabricating MNSDEDs, depending on specific MNSDED end-uses and applications, should be readily apparent to one of ordinary skill. In step 1101, thiol-R-thiol molecules are attached to the surfaces of all the EEBIPs fabricated on the MNSDED. In step 1102, a multilayer protective film stack (MPL), consisting of a photoresist, antireflection coating and bioprotective layer, covers all but one of the EEBIPs, leaving one EEBIP reactive functional handle (thiol) exposed. In step 1103, ssDNA is coupled to the exposed thiol (utilizing, for example, malemide-to-thiol linking chemistry). In step 1104, the MPL is removed from the EEBIPs previously covered in step 1102 utilizing techniques well-known in the art. In step 1105, those EEBIPs already coupled to ssDNA are covered in MPL through standard lithographic techniques, leaving only EEBIPs uncovered that are intended to be coupled with a pre-designed sequence of ssDNA. Steps 1103 through 1105 are repeated until all intended EEBIPs are coupled to ssDNA. In step 1106, after all EEBIPs are coupled to ssDNA, all surfaces are covered in protective layer(s), comprised of biocompatible protective molecules. In step 1107, liftoff trench patterning resist is applied in preparation for separating the MNSDEDs from the silicon wafer using an etch lift-off process.

Figure 12:
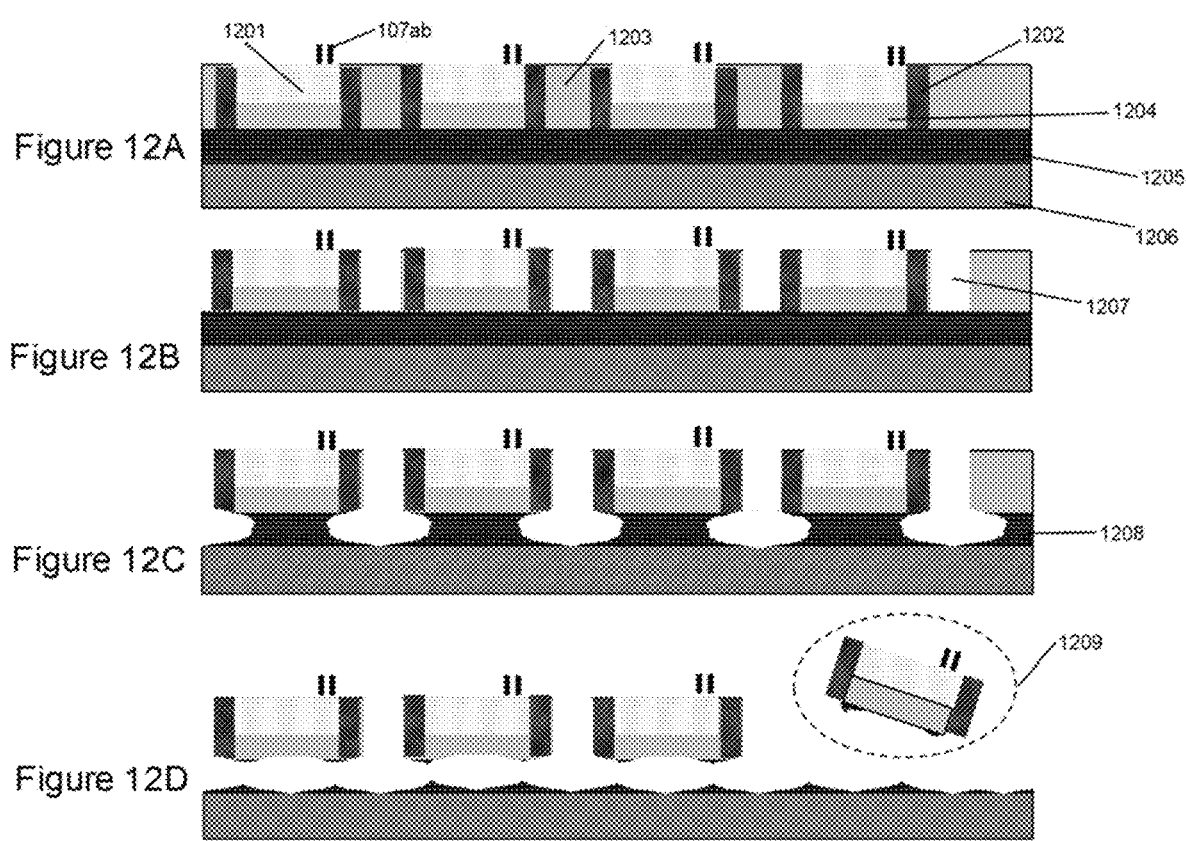
FIGS. 12A-12D illustrate general exemplary steps of bio-compatible lithography and etch lift-off processes to fabricate a MNSDED.

FIGS. 12A-12D are an illustration of an exemplary etch lift-off process used in the fabrication of one or more MNSDEDs. Variations to and deviations from this exemplary etch lift-off process for fabricating MNSDEDs should be readily apparent to one of ordinary skill. In FIG. 12A, each MNSDED region 1201 is surrounded by a well or moat on all four sides of lift-off resistant material 1202, an area 1203 filled with a different material reserved for trench etching, and a bottom layer of each MNSDED 1204. The entire assembly of 1201-1204 is built on a layer of material 1205 which is susceptible to wet-etch attack. The assembly resides on top of a silicon substrate 1206. At this stage of the fabrication process, nanoneedle pair 107 already has been fabricated. MNSDEDs are fabricated and tested on the silicon wafer, and in FIG. 12B, liftoff access trenches 1207 are etched around each MNSDED by removing material 1203 using conventional semiconductor processing (photolithography and etch). This exposes trenches on all four sides of each MNSDED. In FIG. 12C, the silicon wafer is then immersed or otherwise subjected to wet chemistry which enters the now opened trenches 1207, selectively dissolving the underlayer 1205, producing gaps 1208 until the MNSDED bottom layer 1205 is completely dissolved away from underlayer 1206, as depicted in FIG. 12D, and each individual MNSDED 1209 can float away. Alternatively, in a simpler implementation of a lift-off process, layers 1204, 1205 and 1206 may all be part of the silicon substrate. Trenches 1207 are then fabricated with sufficient depth to allow for gaps 1208 to be formed by the wet etch to release the MNSDED 1209 while leaving sufficient material at the bottom of each MNSDED to allow for functional devices.

Figure 13:
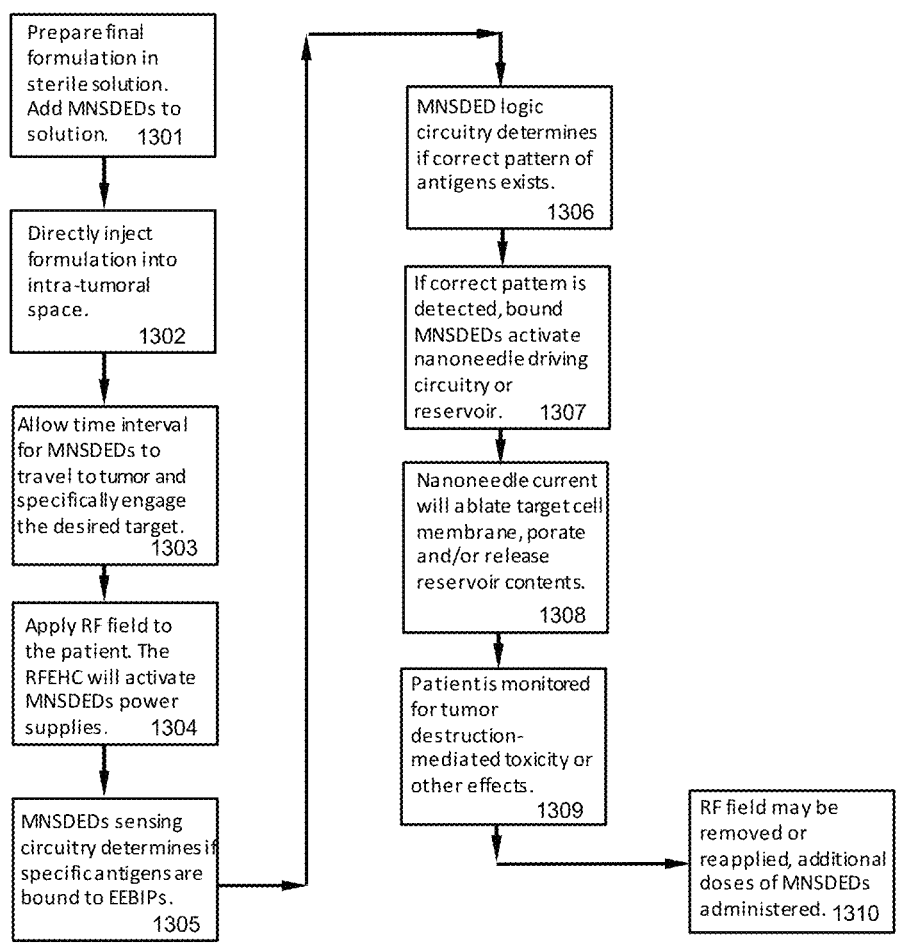
FIG. 13 is a flow diagram describing a proposed exemplary treatment method using a MNSDED system.

FIG. 13 is a flow diagram describing a proposed exemplary treatment method using a MNSDED system. Variations to and deviations from this exemplary treatment method will depend on the specific MNSDED end-use and application. In the embodiment illustrated in FIG. 13, one or more MNSDEDs may be employed in the treatment of solitary brain metastasis from a primary breast cancer ("BMBC"). This flow diagram describes the general steps of formulating one or more MNSDEDs, administering one or more MNSDEDs to a patient, activating the MNSDEDs such that the MNSDED sensing, deciding and effecting subsystems operate as described herein, and monitoring the patient post-treatment.

More specifically, in step 1301, a formulation of sterile solution is prepared and MNSDEDs are added to the sterile solution resulting in the final formulation. In step 1302, the final solution containing the MNSDEDs is then directly injected into the intra-tumoral space of a patient. In step 1303, a period of time is allowed to pass that is sufficient for the MNSDEDs to travel through the tumor and specifically engage the desired target binding molecule. In step 1304, an RF field is applied to the patient. The RF energy is harvested by the RFEHC, supplying power within each of the MNSDEDs. In step 1305, the sensing subsystem circuitry within each of the MNSDEDs generates a signal if specific, predetermined antigens are bound to the EEBIs of the MNSDEDs. In step 1306, the logic circuitry of the deciding subsystem within each MNSDED, based on one or more inputs or signals received from the sensing subsystem, determines if a predetermined (pre-programmed) "correct" pattern of inputs or signals exists, corresponding to a determination that a particular MNSDED is bound to at least one BMBC cell. In step 1307, if the deciding subsystem logic circuitry determines that the MNSDED is bound to at least one BMBC cell, the effecting subsystem is activated, directing current to nanoneedle and/or reservoir associated circuitry. In step 1308, this current is applied to a nano-needle pair that either electro-ablates or electro-porates the BMBC cell membrane, and/or releases the loading compartment or reservoir contents into the BMBC cell. In step 1309, the patient is monitored for tumor destruction-mediated toxicity or other effects. In step 1310, depending on the prescribed treatment regimen, observed effects on the targeted intra-tumoral space, or other factors, the RF field either may be removed to end the treatment, re-applied for a subsequent round of treatment, and/or additional doses of MNSDEDs may be administered to the patient in a manner similar to repeating steps 1302 through 1309.

Figure 14A:
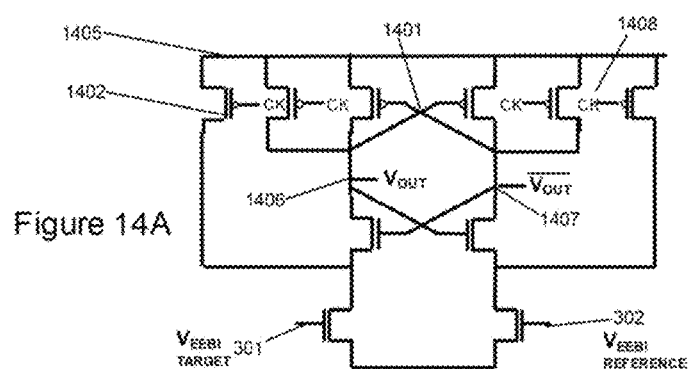
FIGS. 14A-14B show an embodiment of a sense amplifier with associated cross-coupled latch.
Figure 14B:
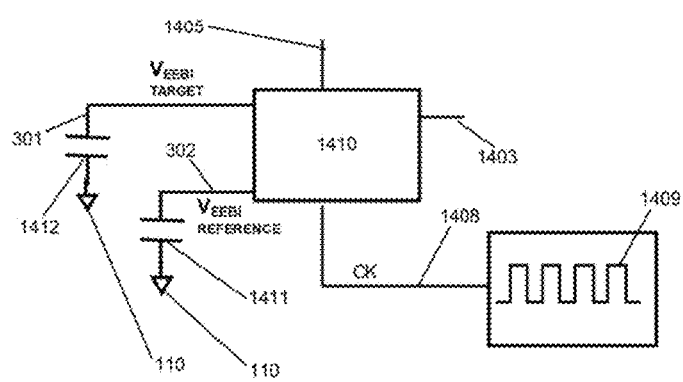

A simple example of a sense amplifier (SA) circuit is illustrated in FIG. 14A. The SA differentially amplifies voltages from a pair of EEBIs, targeting EEBI 301 ($V_{EEBI\ target}$) and reference EEBI 302 ($V_{EEBI\ reference}$) (corresponding to targeting EEBI 301 and reference EEBI 302 in FIG. 3), and incorporates a cross-coupled latch (1401) with output 1406. The SA functions as a comparator, which changes the logical state of its output upon detecting a sufficiently large difference between EEBI 301 and EEBI 302. Changes in capacitance upon binding of a target antigen at the targeting EEBI 301 will induce a voltage difference between the targeting EEBI 301 and the reference EEBI 302, $V_{EEBI\ target} - V_{EEBI\ reference}$, which is amplified and detected by the SA (1410) supplied with clock signal 1408. Clock signal 1408 (node CK) enables NMOS transistor current source 1404 and PMOS current sources 1402 during linear amplification and regenerative amplification phases. Power is applied at 1405 and the output voltage, $V_{out}$, is measured at 1406. The complement of $V_{out}$, $V_{outbar}$ (measured at 1407), is 180 degrees out of phase with $V_{out}$. A latch circuit or other logic elements will be connected to 1406 ($V_{out}$) and 1407 depending on the final detection scheme; variations of this latch circuit will be obvious to those skilled in the art of CMOS comparator design. The output of the latch circuit 1406 represents the binding detection signal. A schematic of a detection circuit incorporating a sense amplifier is represented in FIG. 14B by the sense amplifier 1410, with representative capacitors 1412 and 1411 representing capacitance at the targeting EEBI and reference EEBI, respectively. Power is applied at 1405, and the SA binding signal is output at 1403. Sense amplifier 1410 is clocked from clock circuit 1409 which outputs clock signal 1408. All of the sensing circuitry is referenced to solution-to-bulk silicon connection pad 110.

Figure 15A:
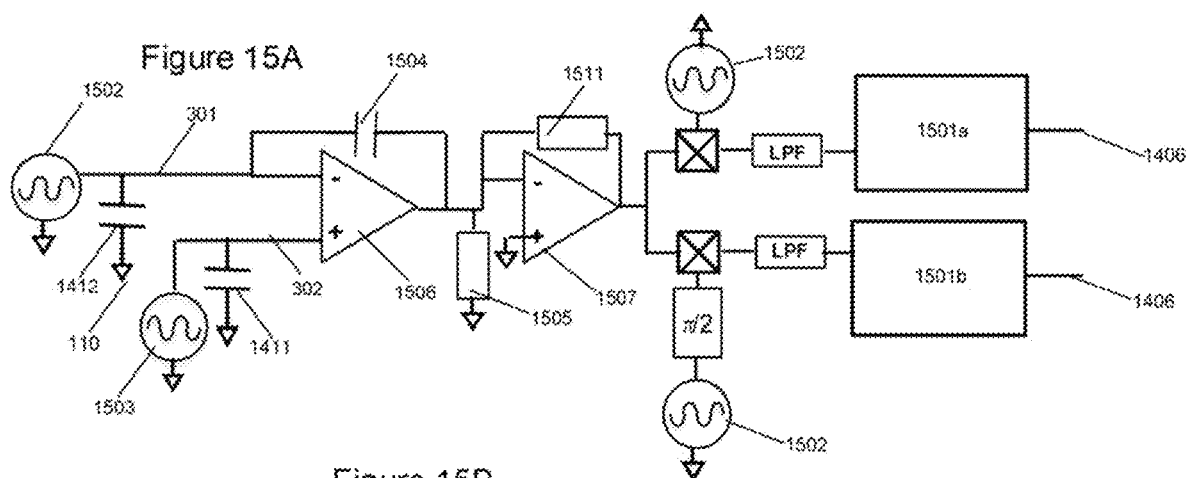
FIGS. 15A-15B show alternative binding detection circuit schemes.
Figure 15B:
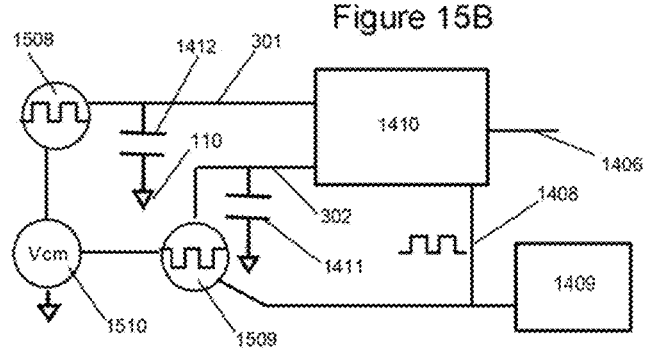

FIGS. 15A-15B illustrate variations of binding detection circuits. FIG. 15A illustrates a linear differential detection scheme where EEBI 301 and 302 with capacitances 1412 and 1411 are driven with oppositely phased AC signals 1502 and 1503 respectively and the resulting currents are subtracted and amplified by a chain of amplifiers 1506 and 1507 with capacitances and/or other impedances 1504, 1507 and 1511 in their feedback paths to create integrating, differentiating, linear or nonlinear amplifiers. The output of amplifier 1507 at the end of the chain is then demodulated using the driving voltage source 1502 and its 90-degree phase shifted replica to create a pair of DC voltages which represent the difference in impedance between target EEBI 301 and its reference EEBI 302. These voltages are then compared to reference thresholds using sense amplifiers 1501*a* and 1501*b*. The outputs from the comparators are fed to sense amplifier output 1406 and used as part of the MNSDED binding detection logic. FIG. 15B illustrates a clocked sense amplifier 1410 used in conjunction with pulsed voltage sources 1508 and 1509 with common mode (bias) voltage source 1510 to impress DC and time-varying voltages onto the EEBI capacitances 1412 and 1411. Upon binding of a target molecule to EEBI 301, variations in the capacitances between the target and reference EEBI 301 and 302 will lead to different discharge rates of 1412 and 1411, leading to a time-varying voltage difference varying with the clock signal 1408 output from clock circuit 1409 which will then be detected by sense amplifier 1410. Variations to and deviations from these exemplary impedance measuring circuits should be readily apparent to one of ordinary skill.

FIGS. 16A-16B illustrate an exemplary schematic representation of the entire MNSDED binding detection process. Variations to and deviations from this exemplary schematic representation of the entire MNSDED binding detection process are possible. In FIG. 16A, EEBITA or target binding molecule 204 and reference molecule 206 are bound to conductive EEBI pads 105*a* and 105*b* via ssDNA 306 and complementary ssDNA 307 in the manner described previously herein (see, e.g., FIG. 3). Each of the EEBI pads 105*a* and 105*b* are electrically connected to sense amplifier ("SA") 1410 (see, e.g., FIGS. 14A-14B or FIGS. 15A-15B), where the SA may include any of the detection methods described in FIGS. 14A-14B and FIGS. 15A-15B, e.g. a clocked comparator, a linear current or voltage amplifier followed by a clocked comparator, a linear amplifier chain followed by demodulation and a clocked comparator or other method for converting the change in capacitance between EEBI 301 and 302 upon a target binding event. SA 1410 is clocked from clock circuit 1409 which outputs clock signal 1408. The voltage output of the SA, $V_{out}$ 1406, is a logic voltage connected to a counting thresholding circuit 1601. In FIG. 16B, if counting thresholding circuit 1601 detects a pre-determined number of affirmative binding events with target antigen(s) 401, corresponding to a pre-determined number of signals 1406 over a pre-determined time interval from SA 1410, it sends a binding signal 1603 to logic circuit 1602. The logic "deciding" circuit 1602 accepts the input from logic circuit 1601 and any other logic inputs which are germane to the binding decision, and activates the nanoneedle driving circuit 801 via nanoneedle driving circuit input signal 1604, supplying a voltage to the nanoneedle pair 107*a-b* and effecting a predetermined effect (e.g., electroablation) on the target cell that was the source of the binding event. Referring back to FIG. 16A, if counting thresholding circuit 1601 fails to detect a pre-determined number of binding events or signals 1406 over a predetermined time interval (corresponding, for example, to the absence of or insufficient target binding) from SA 1410, the signal 1603 to logic circuit 1602 remains unasserted, the corresponding signal to the logic "deciding" circuit 1602 remains quiescent, no signal activates the nanoneedle driving circuit 801, and the nanoneedle pair 107*a-b* remains unpowered.

Figure 17:
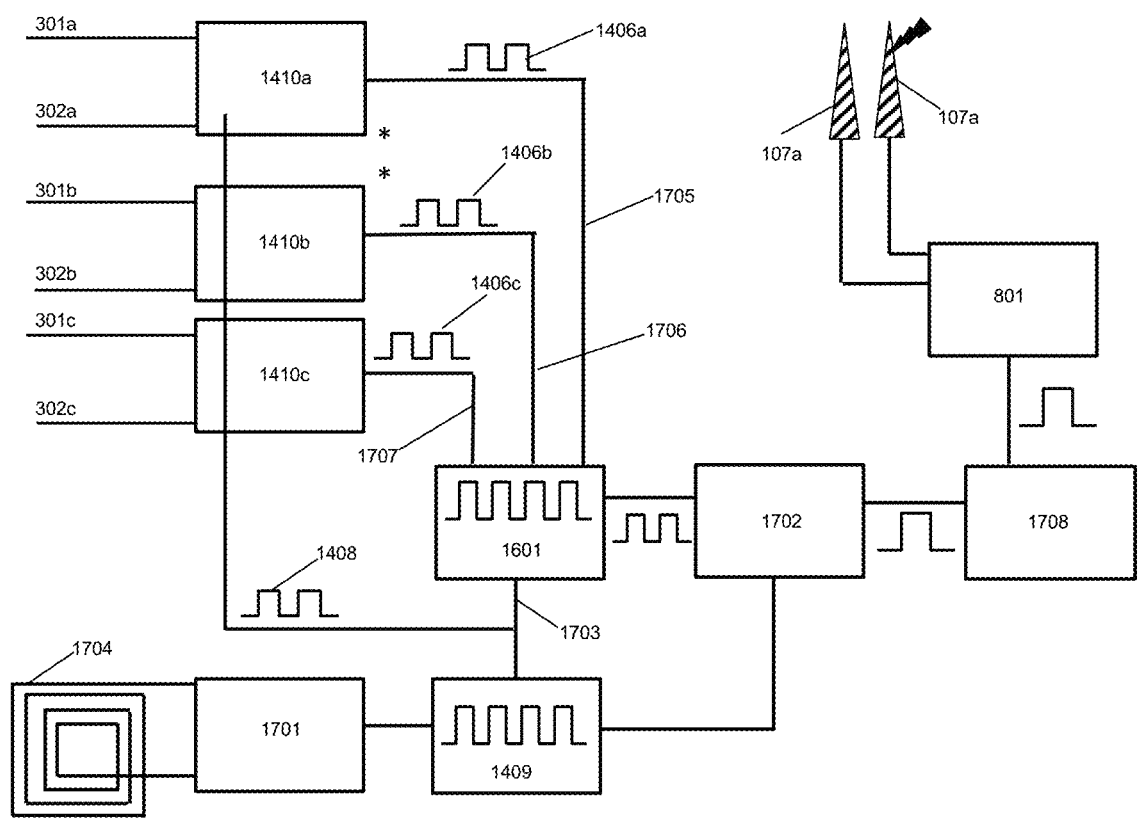
FIG. 17 illustrates a representative diagram of a 3-EEBI pair system.

FIG. 17 illustrates a representative diagram of a 3-EEBI pair system. Variations to and deviations from this exemplary schematic representation of a 3-EEBI pair system are possible. EEBI pairs (301*a*, 302*a*), (301*b*, 302*b*) and (301*c*, 302*c*) include specific EEBITAs and reference molecules. The differential voltage from each EEBI pair is measured by, or input to, clocked sense amplifiers 1410*a*, 1410*b* and 1410*c* respectively. A clock signal 1408 in this embodiment is generated by the same RF that supplies power to the MNSDED; the clock signal is recovered from a RF Energy Harvesting Circuit ("RFEHC") 1701 (including RFEHC coil 1704) and sent to a clock distribution circuit ("CDC") 1409 for distribution throughout the MNSDED on clock lines 1703. The CDC 1409 also supplies counting thresholding circuit 1601 via clock lines 1703. Sense amplifiers 1410*a*, 1410*b* and 1410*c* send their output signals 1406*a*, 1406*b*, and 1406*c* respectively to counting thresholding circuit 1601 via lines 1705, 1706 and 1707 respectively. Counting thresholding circuit 1601 sends each of the received signals 1406*a*, 1406*b*, and 1406*c* (representing binding or non-binding events) to a logic/control circuit 1702, which determines if one or more predetermined patterns, combinations or threshold number of EEBITA binding events has or has not occurred (based on, e.g., a circuit implementation of Boolean logic). If the logic/control circuit 1702 determines that one or more predetermined patterns, combinations or threshold number of EEBITA binding events has occurred, it sends an activation signal via control circuit 1708 to the nanoneedle driving circuit 801 that activates or triggers the nanoneedle pair 107*a-b*. If the logic/control circuit 1702 determines that none of the predetermined patterns, combinations or threshold number of EEBITA binding events has occurred, it withholds sending an activation signal to the nanoneedle driving circuit 801, and the nanoneedle pair 107*a-b* is not activated or triggered.

Figure 18:
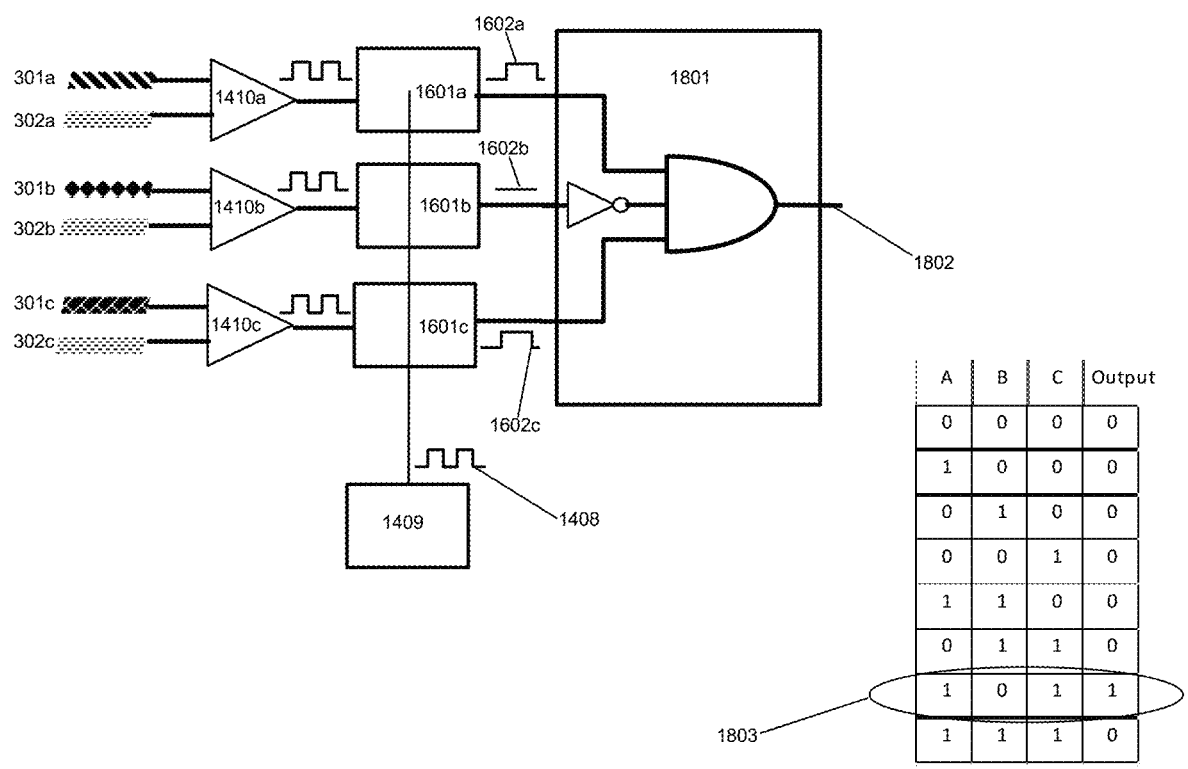
FIG. 18 illustrates an example of a binding pattern decision using a simple logic circuit.

FIG. 18 illustrates an example of a binding pattern decision process using a logic circuit. Variations to and deviations from this exemplary binding pattern decision process are possible. EEBI pairs (301*a*, 302*a*), (301*b*, 302*b*) and (301*c*, 302*c*) include specific EEBITAs and reference molecules. The differential voltage from each EEBI pair is measured by, or input to, clocked sense amplifiers 1410*a*, 1410*b* and 1410*c* respectively. Each clocked sense amplifier 1410*a*, 1410*b* and 1410*c* outputs to a respective clocked counting thresholding circuit 1601*a*, 1601*b* and 1601*c* supplied with a clock signal 1408 from clock distribution circuit 1409. Each counting thresholding circuit outputs a signal 1603*a*, 1603*b* and 1603*c* that are input to a 3-input logic circuit 1801, which implements a logical decision output as a voltage level or signal 1802. This particular 3-input logic circuit embodiment will only trigger the nanoneedle driving circuit 801 (not shown in FIG. 18) via 3-input logic circuit output signal 1802 if counting thresholding circuit output signals 1603*a* and 1603*c* indicate bound antigens but counting thresholding circuit output signal 1603*b* does not, a state indicated by 1803 and circled in the logic table in the lower right of FIG. 18. In this example, counting thresholding circuit output signal 1603*b* may represent an inhibitory binding event. This particular combination of counting thresholding circuit output signals 1603*a*, 1603*b* and 1603*c*, along with all other combinations of counting thresholding circuit output signals not triggering the nanoneedle driving circuit 801, are illustrated in the mapping table in the lower right of FIG. 18. In this particular mapping table, input A corresponds to EEBI pair 301*a* and 302*a* (and its corresponding counting thresholding circuit output signal 1603*a*), input B corresponds to EEBI pair 301*b* and 302*b* (and its corresponding counting thresholding circuit output signal 1603*b*), and input C corresponds to EEBI pair 301*c* and 302*c* (and its corresponding counting thresholding circuit output signal 1603*c*).

FIG. 19 is an exploded perspective view of a multilayer coil Radiofrequency Energy Harvesting Circuit ("RFEHC") 1701 embedded in the MNSDED. Variations to and deviations from this exemplary RFECH design and structure are possible. The first layer of the coil 1901 is shown at the top layer 101 but can be buried in lower layers or be implemented as a multi-turn, multilayer coil with more layers/turns in lower metal/ILD stacks 1902. The coil winding beginning 1903 and coil winding end 1904 are connected to the other elements of the RFEHC in the lower integrated circuit layers of the MNSDED. Each layer of the RFEHC coil is connected to the layers above and below by multiple via structures 1905. The MNSDED is bounded by MNSDED sides 109, which form an isolation well. EEBI pads 105, communications bus pads 106, solution-to-bulk silicon connection pad 110, and nanoneedle pair 107a-b are shown, illustrating that the RFEHC coil 1901 is wrapped outside of the other surface components. Additional buried layers of high-magnetic-susceptibility (high-mu) films 1906 may be placed inside the inner layers of the RFEHC coils.

FIGS. 20A-20C illustrate details of an exemplary RFEHC coil design. Variations to and deviations from this exemplary RFEHC coil design and structure are possible. A single layer, multi-turn planar RFEHC coil is shown in FIG. 20A as 1901 with most of its turns on the outer radii, as the inner radii turns do not intersect as much magnetic flux as the outer radii turns and contribute mostly to loss. The RFEHC coil 1901 may be part of a series or parallel resonant circuit with capacitors associated with a voltage multiplier circuit or connected to a more complex impedance transformation circuit depending on the intended frequency. FIG. 20B illustrates the circuit topology for a multi-layer RFECHC coil 1902, with the start of windings 1903, the termination of the windings 1904, and with the various layers connected in series by via structures 1905. The flux collection efficiency of the coil may be enhanced by placing highly permeable films (with a magnetic susceptibility $\rho \gg \rho_o$, the susceptibility of free space) 1906a, 1906b, 1906c etc. in the interior of one or more of the planar coils, as shown in FIG. 20C. If more than one permeable layer is used, the permeable layers may be connected using via structures made of highly permeable materials 2001.

FIGS. 21A-21B is an example of voltage multiplier circuits connected to RFEHC LC (coil-capacitor) circuits. Variations to and deviations from this example of voltage multiplier circuits connected to RFEHC LC (coil-capacitor) circuits are possible. The RFEHC coil 1901 and capacitor 2101 are connected in series in these examples, but more complex tank circuits could be used as well. In the circuit of FIG. 21A, the RFEHC coil is connected to a Cockcroft-Walton voltage multiplier made of diodes 2103 and capacitors 2102. In the circuit of FIG. 21B, the RFEHC coil is connected to diode-connected MOSFETS 2104. The rectified, multiplied output voltage for both the upper and lower circuits appears at output node 2105.

Figure 22:
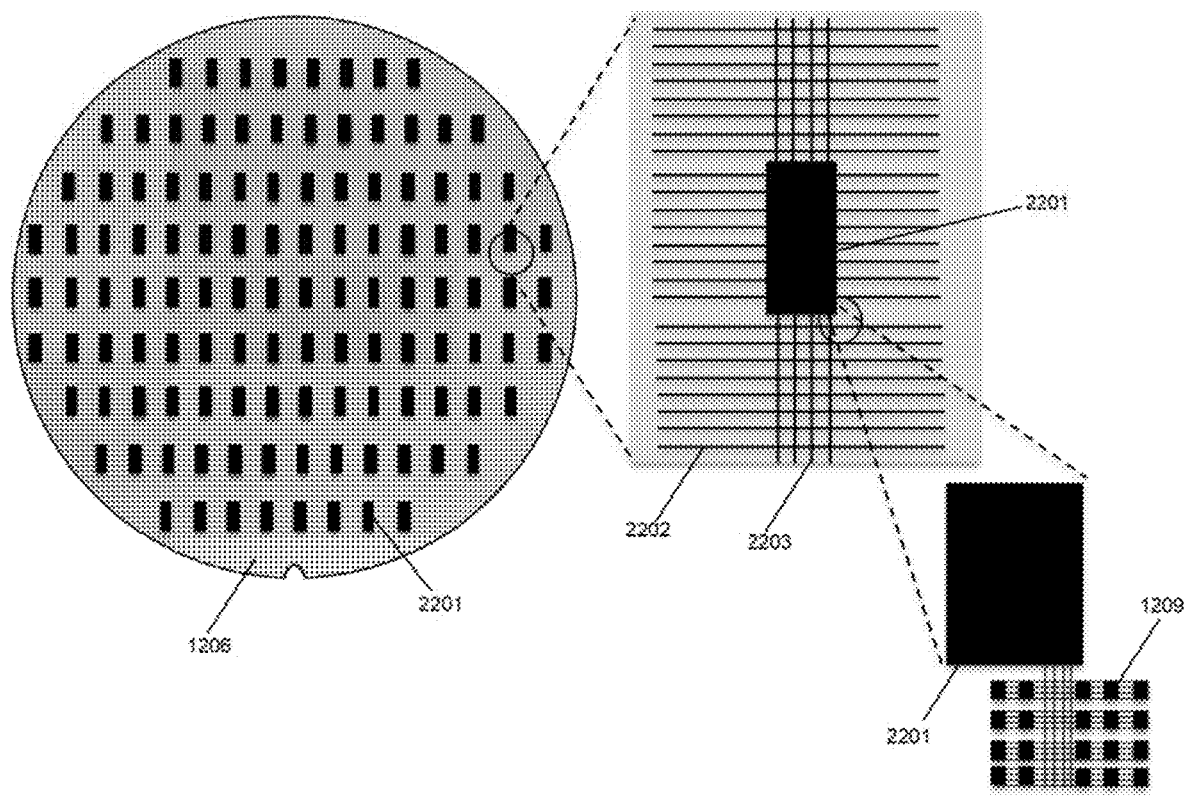
FIG. 22 illustrates an embodiment of a testing method for mass-produced MNSDEDs on a silicon wafer.

FIG. 22 illustrates one possible testing configuration for mass-produced MNSDEDs 1209 fabricated on a silicon wafer 1206. Variations to and deviations from this exemplary testing configuration design and structure are possible. Each MNSDED 1209 is connected to a much larger logic testing chip 2201 over a communication bus with cross-connections 2202 and 2203.

FIGS. 23A-23B is a schema for testing and enabling only those MNSDEDs which pass a set of logic tests to function. Variations to and deviations from this exemplary schema for testing and enabling non-defective MNSDEDs are possible. In FIG. 23A, conductive fusible link 2301 shorts the power delivery circuit 2105 by default in each MNDSED as fabricated. The needle driver 801 of the MNSDED circuitry is represented by the block 2304. If the MNSDED passes the logical test(s) imposed through the logic testing chip 2201 from FIG. 22, then the fusible link 2301 is blown (blown fusible link depicted as 2302 in FIG. 23B) using a current pulse delivered through line 2303, enabling the MNSDED to be powered by the RFECHC. Otherwise the MNSDED remains inert, as in FIG. 23A.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A MNSDED, comprising:
   a non-conductive housing having a surface and that contains supporting logic circuitry;
   at least one electrically conductive needle extending from the housing, with the needle electrically connected to the logic circuitry and to a needle driving circuit;
   at least one electrically conductive pad positioned on the housing surface and electrically connected to the logic circuitry and to at least one targeting agent capable of interacting with a target;
   wherein, in response to target interaction, the logic circuitry allows voltage from the needle driving circuit to be applied to the at least one needle.

2. The MNSDED of claim 1, wherein the non-conductive housing has a major axis length from 100 nanometers to 500 microns and the logic circuitry is manufactured using a 10 nm or less SIA transistor node.

3. The MNSDED of claim 1, further comprising a biocompatible protective agent surrounding at least a portion of the surface of the non-conductive housing.

4. The MNSDED of claim 1, wherein each targeting agent is connected to an electrically conductive linker, with the electrically conductive linker being attached to the electrically conductive pad.

5. The MNSDED of claim 1, wherein the at least one needle is able to interact electrically with a bilipid layer of a target cell that is attached to the targeting agent, and sufficient voltage from the needle driving circuit is available to promote at least one of ablation and electroporation of the target cell.

6. The MNSDED of claim 1, further comprising:
   a reservoir configured in the non-conductive housing to hold at least one of a therapeutic agent and a diagnostic agent;
   wherein, in response to target interaction with the targeting agent, the logic circuitry can initiate release of the at least one of the therapeutic agent and the diagnostic agent.

7. The MNSDED of claim 6, further comprising a release barrier that prevents release of the at least one of the therapeutic agent and the diagnostic agent until electrically activated by the logic circuitry.

8. The MNSDED of claim 7, wherein the release barrier comprises a thermoresponsive material that dissolves when electrically activated by the logic circuitry.

9. The MNSDED of claim 7, wherein the release barrier comprises a material that dissolves when placed in proximity to the target.

10. The MNSDED of claim 1, wherein the at least one electrically conductive pad includes:
- a first electrically conductive pad positioned on the surface and electrically connected both to the logic circuitry and to a first electrically conductive linker that is also attached to a targeting agent capable of interacting with the target; and
- a second electrically conductive pad positioned on the surface and electrically connected both to the logic circuitry and to a second electrically conductive linker that is also attached to a reference agent incapable of interacting with the target,
- wherein, in response to target interaction with the targeting agent, the logic circuitry can initiate an effector mechanism.

11. The MNSDED of claim 10, wherein in response to target interaction with the targeting agent, a sense amplifier connected to the first electrically conductive pad and the second electrically conductive pad is triggered, and deciding logic circuitry can promote at least one of ablation and electroporation of the target or initiate release of at least one of a therapeutic agent and diagnostic agent from a reservoir.

12. The MNSDED of claim 1, further comprising a gasket surrounding the at least one electrically conductive pad.

13. The MNSDED of claim 12, wherein the gasket promotes binding of the targeting agent when the targeting agent interacts with the target.

14. The MNSDED of claim 12 wherein the gasket is formed from molecules that extend longer than molecules forming the biocompatible protective agent.

15. The MNSDED of claim 12, wherein a boundary of the gasket is printed on the MNSDED surface around the at least one electrically conductive pad using bio-safe lithography.

16. The MNSDED of claim 1, further comprising an antenna supported by the non-conductive housing and connected to an energy harvesting circuit to power the logic circuitry and voltage amplifier circuitry.

17. The MNSDED of claim 16, wherein the antenna further comprises a multi-turn and multi-layer coil.

18. The MNSDED of claim 16, wherein the antenna is further connected to signaling circuitry.

19. The MNSDED of claim 1, further comprising an antenna supported by the non-conductive housing and connected to a signaling circuit connected to the logic circuitry.

20. The MNSDED of claim 19, wherein the signaling circuit can enable communication with an external transceiver.

21. The MNSDED of claim 19, wherein the signaling circuit can enable communication with another MNSDED.

22. The MNSDED of claim 1, further comprising:
- at least one electrically conductive linker connecting each targeting agent of the at least one targeting agent with an electrically conductive pad; and
- a biocompatible protective agent surrounding at least a portion of the surface of the non-conductive housing,
- wherein a zeta potential of the MNSDED is between 0 mV and −20 mV.

23. A method of treating disease associated cells (DACs), comprising:
- introducing into a patient a plurality of MNSDEDs, each MNSDED having a non-conductive housing having a surface and that contains supporting logic circuitry and at least one electrically conductive needle extending from the housing, with the needle electrically connected to the logic circuitry and to a needle driving circuit, and further comprising at least one electrically conductive pad positioned on the housing surface and electrically connected to the logic circuitry and a targeting agent capable of interacting with a DAC; and
- in response to DAC and MNSDED interaction via the targeting agent, applying voltage from the needle driving circuit to the at least one needle to ablate the DAC.

24. A therapeutic composition, comprising:
a pharmaceutically acceptable carrier; and
a plurality MNSDEDs contained within the carrier, the MNSDEDs including a non-conductive housing having a surface and that contains supporting logic circuitry; at least one electrically conductive needle extending from the housing, with the needle electrically connected to the logic circuitry and to a needle driving circuit; and at least one electrically conductive pad positioned on the housing surface and electrically connected to the logic circuitry and to a targeting agent capable of interacting with a target.

* * * * *

UNITED STATES PATENT AND TRADEMARK OFFICE
CERTIFICATE OF CORRECTION

PATENT NO. : 11,879,892 B2  
APPLICATION NO. : 16/841456  
DATED : January 23, 2024  
INVENTOR(S) : David Nathan Shykind et al.

Page 1 of 1

It is certified that error appears in the above-identified patent and that said Letters Patent is hereby corrected as shown below:

In the Claims

At Column 48, Line 34, "a plurality" should be -- a plurality of --.

Signed and Sealed this
Fourth Day of March, 2025

Coke Morgan Stewart
*Acting Director of the United States Patent and Trademark Office*